US007179655B2

(12) United States Patent
Patricelli

(10) Patent No.: US 7,179,655 B2
(45) Date of Patent: Feb. 20, 2007

(54) PROTEIN PROFILING PLATFORM

(75) Inventor: Matthew Patricelli, San Diego, CA (US)

(73) Assignee: Activx Biosciences, Inc., La Jolla, CA (US)

( * ) Notice: Subject to any disclaimer, the term of this patent is extended or adjusted under 35 U.S.C. 154(b) by 323 days.

(21) Appl. No.: 10/087,602

(22) Filed: Mar. 1, 2002

(65) Prior Publication Data

US 2002/0182651 A1 Dec. 5, 2002

Related U.S. Application Data

(60) Provisional application No. 60/273,007, filed on Mar. 2, 2001.

(51) Int. Cl.
*G01N 24/00* (2006.01)
(52) U.S. Cl. .................. 436/173; 435/7.1; 435/7.92; 436/175; 436/536; 436/63
(58) Field of Classification Search .............. 435/7.1, 435/7.92, 962, 7.9; 436/518, 524, 536, 63, 436/164, 173, 805, 175
See application file for complete search history.

(56) References Cited

U.S. PATENT DOCUMENTS

| 4,415,655 | A | 11/1983 | de Castro et al. .............. 435/17 |
| 4,433,051 | A | 2/1984 | Gilad et al. ................... 435/7 |
| 4,481,094 | A | 11/1984 | de Castro et al. ....... 204/180 G |
| 4,865,707 | A | 9/1989 | Karger et al. ............ 204/182.8 |
| 4,946,794 | A | 8/1990 | Berube ......................... 436/86 |
| 5,041,538 | A | 8/1991 | Ling et al. .................. 530/395 |
| 5,290,920 | A | 3/1994 | Sindrey et al. ............. 530/412 |
| 5,856,082 | A | 1/1999 | Aebersold et al. ............. 435/4 |
| 6,008,373 | A | 12/1999 | Waggoner et al. .......... 548/427 |
| 6,107,623 | A | 8/2000 | Bateman et al. ............ 250/282 |
| 6,124,137 | A | 9/2000 | Hutchens et al. ........... 436/155 |
| 6,127,134 | A | 10/2000 | Minden et al. .............. 435/7.2 |
| 6,204,500 | B1 | 3/2001 | Whitehouse et al. ....... 250/287 |
| 6,268,144 | B1 | 7/2001 | Koster .......................... 435/6 |
| 6,379,970 | B1 | 4/2002 | Liebler et al. ............... 436/86 |
| 2002/0045194 | A1* | 4/2002 | Cravatt et al. .............. 435/7.9 |
| 2002/0076739 | A1* | 6/2002 | Aebersold et al. ......... 435/7.92 |
| 2002/0150961 | A1* | 10/2002 | Bogyo et al. ................ 435/23 |
| 2003/0003465 | A1* | 1/2003 | Little et al. .................... 435/6 |

FOREIGN PATENT DOCUMENTS

| WO | WO 91/15228 | 10/1991 |
| WO | WO 00/11208 | 3/2000 |
| WO | WO 01/77668 A2 | 10/2001 |
| WO | WO 01/77684 A2 | 10/2001 |

OTHER PUBLICATIONS

Adam et al., "Profiling the specific reactivity of the proteome with non-directed activity-based probes," Chemistry & Biology 2000, 57:1-16, Jan. 2000.

Bergseid et al., "Small molecule-based chemical affinity system for the purification of proteins," BioTechniques, 29:1126-1133, Nov. 2000.
Bogyo et al., "Selective targeting of lysosomal cysteine proteases with radiolabeled electrophilic substrate analogs," Chemistry & Biology 2000, 7:27-38, Dec. 15, 1999.
Clauser et al., "Rapid mass spectrometric peptide sequencing and mass matching for characterization of human melanoma proteins isolated by two-dimensional PAGE," Proc.Natl.Acad.Sci.USA, 92:5072-5076, May 1995.
Cravatt and Sorensen, "Chemical strategies for the global analysis of protein function," Current Opinion in Chemical Biology, 4: 663-668, 2000.
Cull and McHenry, "Preparation of extracts from prokaryotes," *Methods in Enzymology*, vol. 182, 147-238,. 1990 edition.
Daniel et al., "FastTag™ nucleic acid labeling system . . . ," BioTechniques, 24: 484-489, Mar. 1998.
U.S. Appl. No. 10/035,451, Bogyo et al.
DeLeenheer and Thienpont, "Applications of isotope dilution-mass spectrometry in clinical chemistry, pharma-cokinetics, and toxicology," Mass Spectrometry Reviews, 11:249-307, 1992.
Eng et al., "An approach to correlate tandem mass spectral data of peptides with amino acid sequences in a protein database," J.Am. Soc.Mass.Spectrometry, 5:976-989, 1994.
Greenbaum et al., "Epoxide electrophiles as activity-dependent profiling and discovery tools," Chemistry & Biology 2000, 7:569-581, Aug. 1, 2000.
Gygl et al, "Protein analysis by mass spectrometry and sequence database searching: tools for cancer research in the post-genomic era," Electrophoresis, 20: 310-319, 1999.
Gygl et al., "Correlation between protein and mRNA abundance in yeast," Molecular and Cellular Biology, 19: 1720-1730, 1999.
Gygl et al., "Evaluation of two-dimensional gel electrophoresis-based proteome analysis technology," Proc. Nat.Acad.Sci.USA, 97:9390-9395, 2000.
Kasicka, "Recent advances in capillary electrophoresis of peptides," Electrophoresis, 22:4139-4162, 2001.
Kidd et al, "Profiling serine hydrolase activities in complex proteomes," Biochemistry, 40:4005-4015, 2001.
Laemmli, "Cleavage of structural proteins during the assembly of the head of bacteriophage T4," Nature, 227: 680-685, 1970.
Link et al., "Identifying the major proteone components of haemophilus influenzae type-strain NCTC 8143," Electrophoresis, 18: 1314-1334, 1997.

(Continued)

*Primary Examiner*—Long V. Le
*Assistant Examiner*—Gary W. Counts
(74) *Attorney, Agent, or Firm*—Foley & Lardner; Stephen E. Reiter

(57) ABSTRACT

Methods and compositions are described for analyzing complex protein mixtures, such as proteomes, using activity-based probes. In particular, probes that specifically react with and bind to the active form of one or more target proteins are employed. Labeled peptides obtained from the labeled active target proteins can be used in screening and identification procedures, and can be related to the identity, presence, amount, or activity of active members of the desired target protein class. The methods and compositions described herein can be used, for example, to provide diagnostic information concerning pathogenic states, in identifying proteins that may act as therapeutic targets, and in drug discovery.

39 Claims, 3 Drawing Sheets

OTHER PUBLICATIONS

Liu et al., "Activity-based protein profiling: The Serine hydrolases," Proc. Nat. Acad. Sci 1999, 96: 14694-14699, Dec. 21, 1999.

Mann and Wilm, "Error-tolerant identification of peptides in sequence databases by peptide sequence tags," Anal. Chem., 66: 4390-4399, 1994.

Merchant and Weinberger, "Recent advancements in surface-enhanced laser desorption/ionization-time of flight-mass spectrometry," Electrophoresis, 21: 1164-1167, 2000.

Opiteck et al., "Comprehensive two-dimensional high-performance liquid chromatography for the isolation of Overexpressed proteins and proteome mapping," Analytical Biochemistry, 258: 349-361, 1998.

Porco, "Organic synthesis using chemical tags: The "third leg" of parallel synthesis," Combinatorial Chemistry & High Throughput Screening, 3: 93-102, 2000.

Sanchez and Smith, "Capillary electrophoresis," Methods in Enzymology, 289:469-478, 1997.

Wright et al., "Proteinchip® surface enhanced laser desorption/ionization (SELDI) mass spectrometry: a novel Protein biochip technology for detection of prostate cancer biomarkers in complex protein mixtures," Prostate Cancer and Prostatic Diseases, 2: 264-276, 1999.

Xu, "Capillary electrophoresis," Analytical Chemistry, 67: 463R-473R, 1995.

Mills et al., "Identification of a ligand binding site in the human neutrophil formyl peptide receptor using a site-specific fluorescent photoaffinity label and mass spectrometry." The Journal of Biological Chemistry, 273(17): 10428-10435, 1998.

Supplementary European Search Report dated Dec. 13, 2004 for European Patent Application No. 02723286.7-2404-PCT/US0206234.

* cited by examiner

PROTEIN PROFILING PLATFORM

This application claims priority to provisional U.S. Patent Application No. 60/273,007, filed Mar. 2, 2001, which is hereby incorporated by reference in its entirety, including all tables, figures, and claims.

FIELD OF THE INVENTION

The field of this invention is analysis of complex protein mixtures, such as proteomes.

BACKGROUND

The following discussion of the background of the invention is merely provided to aid the reader in understanding the invention and is not admitted to describe or constitute prior art to the present invention.

The biological revolution has progressed from genomics to proteomics as the newest frontier for gathering information concerning cellular physiology. Transcription of DNA is an early step in an extended process resulting ultimately in the expression of genomic information as a functional protein. Additional steps can include processing of the initial transcript to mRNA, translation of the mRNA into protein, and posttranslational processing of the protein (e.g., cleavage of the protein into smaller fragments, modification of the protein by glycosylation, methylation, acylation, phosphorylation, etc.). In addition, the protein may be activated or deactivated by interaction with other proteins and/or with small molecules (e.g., cofactors). Regulation of active protein expression can occur at one or more of these steps, and the amount of active protein in the cell at any time will vary widely with the state of the protein in the cell. Thus, the presence of a given gene in a cell's genome, or the total amount of a particular protein in a cell is not necessarily a good prognosticator of the state of the cell, as reflected by the amount of active protein present in the cell.

In evaluating candidate drugs, the readout should provide an indication how the drug will perform in vivo. For example, an accurate evaluation of a candidate drug can be obtained by using the drug in vivo and determining the effect of the drug on the indication and/or absorption, distribution, metabolism, and excretion ("ADME") studies performed. However, where there are a large number of candidates as are available today from combinatorial libraries, and natural and other sources, substitute procedures must be available to allow for reducing the number of candidate drugs to be studied. To allow for large numbers of candidate drugs to be evaluated, while having reasonable costs and times involved, cellular surrogates are finding use. One can expose cells in culture to candidate drugs. The question then is what should be analyzed to obtain the greatest amount of accurate information relevant to the effect of the drug in the most expedient way.

There is substantial interest in providing platforms that will provide answers to questions asked about the effect of candidate drugs on cells, tissues, and/or organisms. In order for platforms to be useful they should be efficient, reliable, and economic, and maximize the information provided and the predictive capability of the results. The ability to analyze samples in parallel and the reproducibility, speed, automation, sensitivity, and specificity of the analysis procedures can all contribute to maximizing the efficiency and reliability of such a platform.

Numerous methods have been described for analyzing protein compositions. Some typical examples include WO 00/11208, which discusses mass spectrometric methods for analysis of proteins; Cravatt and Sorenson, Current Opinion in Chemical Biology (2000) 4(6): 663–668, which discusses chemical strategies for analyzing protein function; U.S. Pat. No. 4,433,051, which discusses the use of α-difluoromethylomithine for use in protein analysis; U.S. Pat. No. 6,127,134, which discusses difference gel electrophoresis using matched multiple dyes; Gygi et al., Proc. Natl. Acad. Sci. USA (2000) 97:9390–5, which discusses the use of 2D gel electrophoresis in conjunction with mass spectrometry to analyze yeast proteins; and Aebersold et al., PCT/US99/19415, which discusses digestion of labeled protein samples.

Complex protein mixtures, such as proteomes, can be difficult to analyze. Not only are there many components in the mixtures, but as samples of these mixtures may be processed, many artifacts can be introduced into the sample, e.g., by hydrolysis of amide bonds, deamination, oxidation and the like. In addition, proteins present in the mixture that originally derived from the same polypeptide sequence may have been subject to differential processing reactions, such as glycosylations, prenylations, etc. Moreover, in analysis procedures in which the proteins in a complex mixture are subject to proteolysis, the total number of components is greatly increased in comparison to the original sample. As a result, numerous fractions in a chromatography procedure or bands in an electrophoretic gel can be related to a single protein in the original sample, greatly complicating the interpretation of the data. It is of interest to find ways to simplify the compositions that are being analyzed to permit a more accurate and robust interpretation of the observed results.

SUMMARY OF THE INVENTION

Compositions and methods are provided for the identification of active proteins in a complex protein mixture (e.g., a proteomic mixture). In various aspects, the present invention relates to methods for combining one or more complex protein mixture(s) with activity based probes ("ABPs") to produce covalent conjugates of the active target proteins with the probes. The probes comprise a "warhead" (defined hereinafter) directed to a desired protein class covalently linked to a ligand, which may be, directly or indirectly, detectable, e.g. by fluorescence ("fABP"), and which may be used for separation and/or detection. Optionally, the ligand may be used for enrichment of the conjugates.

Following reaction of the complex protein mixture with one or more ABPs, the resulting protein conjugates are proteolytically digested to provide probe-labeled peptides. In preferred embodiments, ABPs are selected such that each active target protein forms a conjugate with a single ABP, most preferably at a single discrete location in the target protein; thus, each conjugate gives rise to a single ABP-labeled peptide. Enrichment separation, or identification of one or more ABP-labeled peptides may be achieved using liquid chromatography arid/or electrophoresis. Additionally, mass spectrometry may be employed to identify one or more ABP-labeled peptides by molecular weight and/or amino acid sequence. In particularly preferred embodiments, the sequence information derived from of the ABP-labeled peptide(s) is used to identify the protein from which the peptide originally derived. Variations of these aspects can involve the comparison of two or more proteomes, e.g., with ABPs having different ligands, or, when analysis comprises mass spectrometry, having different isotopic compositions.

Thus, in a first embodiment, the invention relates to methods for determining the presence amount, or activity of one or more active target proteins in a complex protein mixture, most preferably a proteome. In various embodiments, these methods comprise one or more of the following steps: contacting a complex protein mixture with an ABP that specifically binds to one or more active target proteins present in the complex protein mixture; proteolyzing the active target protein(s) to produce a product mixture comprising ABP-labeled peptides; separating the resulting product mixture into one or more of its component parts, where one or more of these components comprise one or more ABP-labeled peptides; and generating a signal from those peptides bound to the ABP. Such a signal can be correlated to the presence, amount, or activity of one or more active target proteins present in the original complex protein mixture.

In preferred embodiments, ABP(s) and reaction conditions are selected such that the relative ability of an active target protein to become labeled depends on the relative level of activity of that active target protein; the signal obtained from such labeling can be correlated to the activity of the active target proteins in the proteomic mixture. Alternatively, ABPs can be used under conditions in which all active forms of an active target protein are labeled, regardless of the level of activity of the particular active target protein. For example, the time of reaction may be extended so that the labeling reaction goes substantially to completion; the signal obtained from such labeling will be unrelated to the activity of the active target proteins in the proteomic mixture.

Similarly, in a second embodiment, the instant invention relates to methods for comparing the presence or amount of one or more active target proteins in two or more complex protein mixtures. In various embodiments, these methods comprise one or more of the following steps: contacting one or more complex protein mixture(s) with one or more ABPs, where the ABP(s) specifically bind to one or more active target proteins present in each complex protein mixture; combining the complex protein mixtures following this contacting step to form a combined complex protein mixture; proteolyzing the active target protein(s) in the complex protein mixture(s) to produce one or more product mixtures comprising ABP-labeled peptides; separating the resulting product mixture(s) into one or more component parts, where one or more of these components comprise one or more ABP-labeled peptides; and comparing the signals generated from corresponding ABP-labeled peptides originating from each original complex protein mixture.

In preferred embodiments, the ABP(s) comprise a ligand that can be used to identify those ABP-labeled peptides originating from a particular original complex protein mixture (e.g. two ABPs comprising the same warhead but different fluorescent moieties can be used to label two different complex protein mixtures).

In additional preferred embodiments, the methods further comprise one or more of the following: the separating step comprises sequestering one or more ABP-peptide conjugates using a receptor that specifically binds to said probe; the ABP(s) used comprise a fluorescent moiety, and the receptor is an antibody or antibody fragment that binds to the fluorescent moiety; the ABP(s) used comprise a fluorescent moiety, and the signal generated is a fluorescent signal; the signal generated is a mass spectrum; the ABP(s) used comprise an isotopic label; the separating step(s) employed comprise one or more separation methods selected from the group consisting of affinity separation, gel electrophoresis, capillary electrophoresis, liquid chromatography, HPLC, electrospray ionization and MALDI; one or more active target proteins bound to said probe are bound to a solid support prior to proteolysis; one or more standard proteins are added to the complex protein mixture prior to proteolysis; the standard protein(s) are labeled with an activity based probe prior to addition to the complex protein mixture; the standard protein(s) are labeled with an ABP comprising a fluorescent moiety that is distinguishable from the ABP(s) contacted with complex protein mixture.

Additionally, in particularly preferred embodiments, the methods described herein include a step in which, prior to proteolysis, one or more components of the complex protein mixture not bound to an ABP are removed. This can be accomplished, for example, by sequestering ABP-active target protein conjugates (e.g., by binding conjugates to a solid phase, and washing out the remaining, unbound, components of the complex protein mixture). The conjugates can then be proteolyzed either while sequestered (e.g., bound to a solid phase), or following release into solution.

In another aspect, the present invention relates to methods and compositions for correlating a separation profile to a peptide having a known sequence using ABPs. In these methods, a separation profile is generated for the ABP-bound peptide by performing one or more separation methods, and generating a signal from the ABP-bound peptide. A separation profile that is characteristic of the peptide having said known sequence can be used to identify the peptide in subsequent separation procedures.

In various preferred embodiments, these methods comprise one or more of the following steps: contacting a protein sample comprising the peptide with an ABP that specifically binds to said amino acid sequence; proteolyzing the protein sample to produce a product mixture; separating peptides bound to the ABP from said product mixture; generating a mass spectrum from the peptides bound to the ABP to provide sequence information for the peptide; and generating a separation profile by capillary electrophoresis of peptides bound to said probe, where the separation profile is one or more migration time(s) of peptides bound to the ABP.

DESCRIPTION OF THE SPECIFIC EMBODIMENTS

Figure 1:
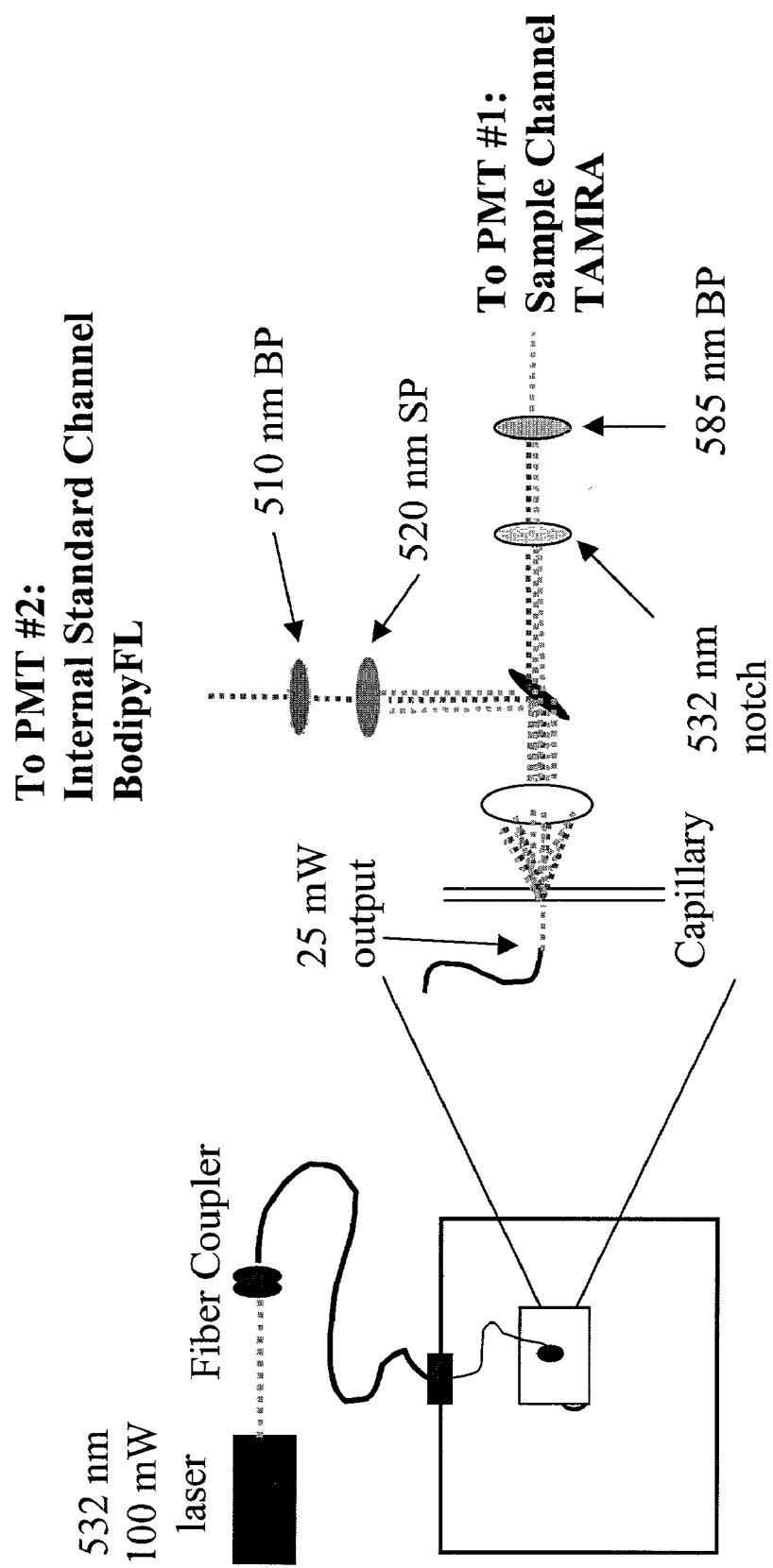
FIG. 1 is a schematic drawing of a typical capillary electrophoresis—laser induced fluorescence instrument configuration to provide dual channel fluorescence detection. In the figure, "PMT" refers to the photomultiplier tube of a detector; "BP" refers to a band pass filter; "SP" refers to a short pass filter (a filter that passes shorter wavelengths), and "notch" refers to a notch filter.

The subject methods and compositions provide enhanced simplicity and accuracy in identifying changes in active protein composition of a complex protein mixture. Using ABPs that bind to active target proteins, the analysis of complex protein mixtures may be greatly simplified, particularly by providing ABPs that bind to active target proteins at a single site. The proteins are then proteolytically digested, resulting in a single representative ABP-labeled peptide fragment from each of the conjugates. Using various approaches to identification of the ABP-labeled peptide(s), the protein(s) from which each ABP-labeled peptide originally derived can be identified.

The protein profiling platforms described herein can have a number of steps leading to the identification of active target proteins in a complex protein mixture. A complex protein mixture, and preferably two or more complex protein mixtures, e.g., a sample and a control, can be used as obtained from a natural source or as processed, e.g., to remove interfering components and/or enrich the target protein components. Each proteomic mixture to be analyzed is combined under reaction conditions with at least one ABP to produce conjugates with active target proteins. The ABPs used in two or more complex protein mixtures can differ as to the choice of ligand moiety and/or isotopic composition in order for the labeled complex protein mixtures to be directly compared (e.g., in the same capillary of a capillary electrophoresis apparatus or lane in an electrophoresis gel, or in a mass spectrometer). Additionally the ligand moiety can be used to sequester the conjugate(s) and remove unlabeled components from the complex protein mixture(s) or proteolytic product mixture(s).

As described herein, the labeled ABP-active target protein conjugates are most preferably proteolytically digested prior to the next stage of enrichment and/or analysis. While the skilled artisan would expect that proteolytic digestion would lead to a more complex protein mixture, the methods of the instant invention demonstrates that such proteolysis can actually provide an advantageous simplification of the complex protein mixture during subsequent analysis.

The analysis platforms described herein differ as to the methods of enrichment and analysis using liquid chromatography and/or electrophoresis, and/or mass spectrometry for identification and quantitation. The choice of the platform is affected by the size of the sample, the rate of throughput of the samples, the mode of identification, and the need for and level of quantitation.

The compositions and methods described herein find use for the most part with biological samples, which may have been subject to processing before reaction with the ABPs. "Biological sample" intends a sample obtained from a cell, tissue, or organism. Examples of biological samples include proteins obtained from cells (e.g., mammalian cells, bacterial cells, cultured cells), particularly as a lysate, a biological fluid, such as blood, plasma, serum, urine, bile, saliva, tears, cerebrospinal fluid, aqueous or vitreous humor, or any bodily secretion), a transudate or exudate (e.g. fluid obtained from an abscess or other site of infection or inflammation), a fluid obtained from a joint (e.g. a normal joint or a joint affected by disease such as rheumatoid arthritis, osteoarthritis, gout or septic arthritis), or the like.

Biological samples may be obtained from any organ or tissue (including a biopsy or autopsy specimen) or may comprise cells (including primary cells, passaged or cultured primary cells, cell lines, cells conditioned by a specific medium) or medium conditioned by cells. In preferred embodiments, a biological sample is free of intact cells. If desired, the biological sample may be subjected to prior processing, such as lysis, extraction, subcellular fractionation, and the like. See, Deutscher (ed.), 1990, Methods in Enzymology, vol. 182, pp. 147–238.

Of particular interest are samples that are "complex protein mixtures." As used herein, this phrase refers to protein mixtures having at least about 20, more usually at least about 50, even 100 or more different proteins, where the particular distribution of proteins is of interest. An example of such a complex protein mixture is a proteome, as defined hereinafter. Complex protein mixtures may be obtained from cells that are normal or abnormal in some particular, where the abnormality is informative as to treatment, status, disease, or the like, can be analyzed using the methods of the subject invention.

The term "proteome" as used herein refers to a complex protein mixture obtained from a biological sample. Preferred proteomes comprise at least about 5% of the total repertoire of proteins present in a biological sample (e.g., the cells, tissue, organ, or organism from which a lysate is obtained; the serum or plasma, etc.), preferably at least about 10%, more preferably at least about 25%, even more preferably about 75%, and generally 90% or more, up to and including the entire repertoire of proteins obtainable from the biological sample. Thus the proteome may be obtained from an intact cell, a lysate, a microsomal fraction, an organelle, a partially extracted lysate, biological fluid, and the like. The proteome will be a mixture of proteins, generally having at least about 20 different proteins, usually at least about 50 different proteins and in most cases 100 different proteins or more.

Generally, the sample will have at least about $1\times10^{-11}$ g of protein, and may have 1 g of protein or more, preferably at a concentration in the range of about 0.1–50 mg/ml. For screening applications, the sample will typically be between about $1\times10^{-11}$ g and about $1\times10^{-3}$ g of protein, preferably between about $1\times10^{-6}$ g and $1\times10^{-4}$ g of protein. For identification of labeled active target proteins, the sample will typically be between about $1\times10^{-9}$ g and about 1 g of protein, preferably between about $1\times10^{-4}$ g and $1\times10^{-1}$ g of protein. The term "about" in this context refers to +/−10% of the amount listed.

The sample may be adjusted to the appropriate buffer concentration and pH, if desired. One or more ABPs may then be added, each at a concentration in the range of about 1 nM to 20 mM, preferably 10 nM to 1 mM, most preferably 10 nm to 100 μM. After incubating the reaction mixture, generally for a time for the reaction to go substantially to completion, generally for about 0.11–60 minutes, at a temperature in the range of about 5–40° C., preferably about 10° C. to about 30° C., most preferably about 20° C., the reaction may be quenched.

In one aspect of the invention, the method provides for quantitative measurement of active target proteins in biological fluids, cells or tissues. Moreover, the same general strategy can be broadened to achieve the proteome-wide, qualitative and quantitative analysis of the state of activity of proteins, by employing ABPs with differing specificity for reaction with proteins. The methods and compositions of this invention can be used to identify proteins of low abundance that are active in complex protein mixtures and can be used to selectively analyze specific groups or classes of proteins, such as membrane or cell surface proteins, or proteins contained within organelles, sub-cellular fractions, or biochemical fractions such as immunoprecipitates. Further, these methods can be applied to analyze differences in expressed proteins in different cell states. For example, the methods and reagents herein can be employed in diagnostic assays for the detection of the presence or the absence of one or more active proteins indicative of a disease state, such as cancer.

The subject method can be used for a variety of purposes. The method can be used in the diagnosis of disease, the response of cells to an external agent, e.g. a drug, staging diseases, such as neoplasia, identifying cell differentiation and maturation, identifying new proteins, screening for active drugs, determining side effects of drugs, identifying allelic response, identifying useful probes from combinatorial libraries, etc.

The system uses ABPs specific for the active form of a protein or a defined group of proteins, usually directed to an active site on such proteins, and combines one or a mixture of probes, depending on the specificity of the probes and the variety in the group or groups of related proteins to be assayed. In the present invention, it is not necessary that there be no reaction of an ABP with inactive target protein(s). Rather, an ABP is defined as being "specific for," as "specifically reacting with," or as "specifically binding to," active target protein(s) if the ABP provides at least about twice the amount of signal from ABP labeling of active protein when compared to an equivalent amount of inactive target protein. Preferably the signal obtained from active target protein(s) will be at least about five fold, preferably 10 fold, more preferably 25-fold, even more preferably 50-fold, and most preferably 100-fold or more, greater than that obtained from an equivalent amount of inactive target protein.

The term "target protein" as used herein refers to one or more proteins, an active site of which becomes labeled by one or more ABPs when the target protein is in its "active" form. The reaction mixture can provide conditions under which the ABP(s) react substantially preferentially with active target proteins. Particularly preferred target proteins are enzymes; other preferred target proteins include receptors, transcription factors, G-proteins, and the like.

The term "active target protein" refers to a target protein that is in its native conformation and is able to interact with an entity with which it normally interacts, e.g. enzyme with substrate and cofactor, receptor with ligand, etc., e.g. phosphorylated active form as compared to unphosphorylated inactive form and vice versa. In effect, the protein is in the form in which it can carry out its biological function.

The term "inactivated" as used herein refers to a sample that has been treated so that at least a portion of target proteins that were active in the original sample are rendered inactive. An "inactive protein" can result from various mechanisms such as denaturation, inhibitor binding, either covalently or non-covalently, mutation, secondary processing, e.g. phosphorylation or dephosphorylation, etc. Functional states of proteins or enzymes as described herein may be distinct from the level of abundance of the same proteins or enzymes. Inactivated samples may be used to validate the activity-specific binding of ABPs as described herein.

The term "untreated" as used herein refers to a sample that has not been exposed to one or more conditions as compared to a second sample not exposed to such conditions. An untreated sample may be a sample that has not been inactivated; alternatively, an untreated sample may be one not exposed to one or more molecules (e.g., drug lead compounds) in a screening assay. Thus the compostions and methods described herein may comprise comparing a complex protein mixture obtained from cell(s), tissue(s), or organism(s) treated with one or more compounds (e.g., lead compounds in drug discovery) to a complex protein mixture obtained from cell(s), tissue(s), or organism(s) not so treated. ABP-labeled peptides from the two samples may be compared for relative signal intensity. Such methods may indicate alterations in active protein content due to the treatment regimen. Additionally, such methods can also differentiate between treatments that act by direct inhibition of specific proteins ("primary effects") versus treatments that affect active protein content upstream, e.g., by altering expression of protein(s) ("secondary effects").

An "active site" of a protein refers to an area on the surface of a protein, e.g., an enzyme molecule or surface membrane receptor, to which a binding molecule, e.g. substrate or reciprocal ligand, is bound and results in a change in the protein and/or ligand. For a receptor, the conformation may change, the protein may become susceptible to phosphorylation or dephosphorylation or other processing. For the most part, the active site will be the site(s) of an enzyme where the substrate and/or a cofactor bind, where the substrate and cofactor undergo a catalytic reaction; where two proteins form a complex, e.g. the site at which a G protein binds to a surface membrane receptor, two kringle structures bind, sites at which transcription factors bind to other proteins; or sites at which proteins bind to specific nucleic acid sequences, etc.

In referring to affinity for an ABP to a target protein, one is concerned with the on-rate of the ABP with the target protein, since there is a negligible off-rate, where the ABP covalently bonds to the target protein. One can determine relative on-rates between ABPs by having less than a stoichiometric amount of the target protein as compared to the total amount of one or more ABPs and then measuring the relative amounts of the conjugates for each of the ABPs. In this way one can obtain a measure of the relative activity of each of the ABPs toward the active target protein, which for the purposes of this invention may be considered the affinity, if not the binding affinity, of the ABP for the target protein.

Exemplary target proteins include enzymes, such as oxidoreductases, hydrolases, ligases, isomerases, transferases, and lyases (and including such enzymes or enzyme groups as serine hydrolases, metallo-hydrolases, dehydrogenases, e.g. alcohol and aldehyde dehydrogenases, and nucleotide triphosphate (NT)-dependent enzymes), although, the invention envisions ABPs which recognize any protein, e.g., enzyme, family. Other target proteins include proteins that bind to each other or to nucleic acids, such as transcription factors, kringle structure containing proteins, nucleic acid binding proteins, G-protein binding receptors, cAMP binding proteins, etc.

Structure of ABPs

The ABPs of the present invention comprise a warhead, linked via a linker moiety to a ligand. Suitable ABPs for use in the invention are disclosed generally, for example, in the following: PCT Application No. PCT/US99/19415, WO 00/11208, entitled "Rapid Quantitative Analysis of Proteins or Protein Function in Complex Mixtures"; PCT Application No. PCT/US00/34187, WO 01/77684, entitled "Proteomic Analysis"; PCT Application No. PCT/US00/34167, WO 01/77668, entitled "Proteomic Analysis"; U.S. Provisional Application No. 60/266,687, entitled, "Activity Based Probe Analysis," filed Feb. 5, 2001; PCT Application No. PCT/US02/03808, WO 02/063271, entitled "Activity Based Probe Analysis", filed Feb. 5, 2002; each of which is hereby incorporated by reference in their entirety, including all tabes, figures, and claims.

As will be described hereinafter, each of the warhead, the linker moiety ("L"), and the ligand ("X") may be independently selected to provide different target specificities. Each of these components of an ABP is described in additional detail below.

The term "warhead" as used herein refers to the portion of an ABP that is directed to and binds with an active site of an active target protein. The warhead comprises a functional group ("F") and an optional affinity moiety ("R"). Functional group (F) refers to one or more chemical groups within an ABP that specifically and covalently bond to the active site of a protein. The functional group may, by its very structure, be directed to the active site of a target protein. Alternatively, a separate affinity moiety (R) may be provided. Affinity moiety (R) refers to a chemical group, which may be a single atom, that is conjugated to the functional group or associated with the linker moiety that provides enhanced binding affinity for protein targets and/or changes the binding profile of the warhead. The affinity moiety is preferably less than 1 kilodalton in mass.

The term "linker moiety" refers to a bond or chain of atoms used to link one moiety to another, serving as a covalent linkage between two or more moieties.

The term "ligand" as used herein refers to a molecule that can be used to detect and/or capture the ABP in combination with any other moieties that are bound strongly to the ligand, so as to be retained in the process of the reaction of the functional group with the target active protein. The ligand may be added to the warhead-linker moiety combination after reaction with the target protein, to form the complete ABP. For this purpose, the warhead-linker moiety combination will include a chemically reactive functionality, normally not found in proteins, that will react with a reciprocal functionality on the ligand, e.g. vic.-diols with boronic acid, photoactivated groups, such as diazo bisulfites, etc. The warhead-linker moiety is then reacted with the ligand to complete the ABP.

The ABP will have an affinity for an active site, which may be specific for a particular active site or generally shared by a plurality of related proteins. The affinity may be affected by the choice of the functional group, the linker moiety, the binding moiety, the ligand, or a combination thereof. As described hereinafter, one or more ABPs may be designed that exhibit specificity for a single target protein, or that exhibit specificity for a plurality of targets that may be structurally or functionally related.

The ABPs of the subject invention may be illustrated by the following formula:

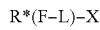

where * indicates that R may be optionally present, and L, if present, may be bound to either F, L or both F and L.

Exemplary Fs as used in an ABP of the invention include an alkylating agent, acylating agent, ketone, aldehyde, sulphonate or a phosphorylating agent. Examples of particular Fs include, but are not limited to fluorophosphonyl, fluorophosphoryl, fluorosulfonyl, alpha-haloketones or aldehydes or their ketals or acetals, respectively, alpha-haloacyls, nitriles, sulfonated alkyl or aryl thiols, iodoacetylamide group, maleimides, sulfonyl halides and esters, isocyanates, isothiocyanantes, tetrafluorophenyl esters, N-hydroxysuccinimidyl esters, acid halides, acid anhydrides, unsaturated carbonyls, alkynes, hydroxamates, alpha-halomethylhydroxamates, aziridines, epoxides, or arsenates and their oxides. Sulfonyl groups may include sulfonates, sulfates, sulfinates, sulfamates, etc., in effect, any reactive functionality having a sulfur group bonded to two oxygen atoms. Epoxides may include aliphatic, aralkyl, cycloaliphatic and spiro epoxides, the latter exemplified by fumagillin, which is specific for metalloproteases.

The linker moiety L, which potentially can be as short as a covalent bond, is preferred to be other than a bond. Since in many cases, the synthetic strategy will be able to include a functionalized site for linking, the functionality can be taken advantage of in choosing the linking moiety. The choice of linker moiety has been shown to alter the specificity of an ABP. See, e.g., Kidd et al., *Biochemistry* (2001) 40: 4005–15. For example, an alkylene linker moiety and a linker moiety comprising a repeating alkyleneoxy structure (polyethylene glycols, or "PEG"), have distinct specificities and provide distinct protein profiles. Thus, one of skill in the art can select the linker moiety of the ABP in order to provide additional specificity of the ABP for a particular protein or protein class.

Linker moieties include among others, ethers, polyethers, diamines, ether diamines, polyether diamines, amides, polyamides, polythioethers, disulfides, silyl ethers, alkyl or alkenyl chains (straight chain or branched and portions of which may be cyclic) aryl, diaryl or alkyl-aryl groups, having from 0 to 3 sites of aliphatic unsaturation. While normally amino acids and oligopeptides are not preferred, when used they will normally employ amino acids of from 2–3 carbon atoms, i.e. glycine and alanine. Aryl groups in linker moieties can contain one or more heteroatoms (e.g., N, O or S atoms). The linker moieties, when other than a bond, will have from about 1 to 60 atoms, usually 1 to 30 atoms, where the atoms include C, N, O, S, P, etc., particularly C, N and O, and will generally have from about 1 to 12 carbon atoms and from about 0 to 8, usually 0 to 6 heteroatoms. The number of atoms referred to above are exclusive of hydrogen in referring to the number of atoms in a group, unless indicated otherwise.

Linker moieties may be varied widely depending on their function, including alkyleneoxy and polyalkyleneoxy groups, where alkylene is of from 2–3 carbon atoms, methylene and polymethylene, polyamide, polyester, and the like, where individual monomers will generally be of from 1 to 6, more usually 1 to 4 carbon atoms. The oligomers will generally have from about 1 to 10, more usually 1 to 8 monomeric units. The monomeric units may be amino acids, both naturally occurring and synthetic, oligonucleotides, both naturally occurring and synthetic, condensation polymer monomeric units and combinations thereof The ligand portion permits capture of the conjugate of the target protein and the probe. The ligand may be displaced from the capture reagent by addition of a displacing ligand, which may be free ligand or a derivative of the ligand, or by changing solvent (e.g., solvent type or pH) or temperature or the linker may be cleaved chemically, enzymatically, thermally or photochemically to release the isolated materials (see discussion of the linker moiety, below).

Examples of ligands, X, include, but are not limited to, detectable labels such as fluorescent moieties and electrochemical labels, biotin, digoxigenin, maltose, oligohistidine, 2,4-dintrobenzene, phenylarsenate, ssDNA, dsDNA, a polypeptide, a metal chelate, and/or a saccharide. Examples of ligands and their capture reagents also include but are not limited to: dethiobiotin or structurally modified biotin-based reagents, including deiminobiotin, which bind to proteins of the avidin/streptavidin family, which may, for example, be used in the forms of strepavidin-Agarose, oligomeric-avidin-Agarose, or monomeric-avidin-Agarose; any vicinal diols, such as 1,2-dihydroxyethane (HO—CH$_2$—CH$_2$—OH), and other 1,2-dihyroxyalkanes including those of cyclic alkanes, e.g., 1,2-dihydroxycyclohexane which bind to an alkyl or aryl boronic acid or boronic acid esters, such as phenyl-B(OH)$_2$ or hexyl-B(OEthyl)$_2$ which may be attached via the alkyl or aryl group to a solid support material, such as Agarose; maltose which binds to maltose binding protein (as well as any other sugar/sugar binding protein pair or more generally to any ligand/ligand binding protein pairs that has properties discussed above); a hapten, such as the dinitrophenyl group, to which an antibody can be generated; a ligand which binds to a transition metal, for example, an oligomeric histidine will bind to Ni(II), the transition metal capture reagent may be used in the form of a resin bound chelated transition metal, such as nitrilotriacetic acid-chelated Ni(II) or iminodiacetic acid-chelated Ni(II); glutathione which binds to glutathione-S-transferase. For the most part, the ligands will be haptens that bind to a naturally occurring receptor, e.g. biotin and avidin, or an antibody or will be a detectable label, that is also a hapten.

One may use chemical affinity resins, e.g. metal chelates, to allow for digestion of proteins on the solid phase resin and facilitate automation. One example of this is the use of immobilized nickel (II) chelates to purify peptides that have six consecutive histidine residues (His-6 tag) (as described in the Invitrogen product brochureProBond™ Resin (Purification) Catalog nos. R801-01, R801-15 Version D 000913 28-0076), which could be adapted to include non-peptidic chemical linkage coupling a series of imidazole-containing moieties. Alternative chemical attachments include phenyldiboronic acids (described in Bergseid, M. et al. Biotechniques (2000) 29(5), 1126–1133), and disulfide reagents (described in Daniel, S M et al., Biotechniques (1998) 24(3), 484–489). Additionally, chemical affinity tags that are useful in combinatorial synthesis could be adapted for modified peptide purification (reviewed in Porco, J A (2000) Comb. Chem. High Throughput Screening 3(2) 93–102.

The term "fluorescent moiety" refers to a ligand that can be excited by electromagnetic radiation, and that emits electromagnetic radiation in response in an amount sufficient to be detected in an assay. The skilled artisan will understand that a fluorescent moiety absorbs and emits over a number of wavelengths, referred to as an "absorbance spectrum" and an "emission spectrum." A fluorescent moiety will exhibit a peak emission wavelength that is a longer wavelength than its peak absorbance wavelength. The term "peak" refers to the highest point in the absorbance or emission spectrum.

The fluorescent moiety may be varied widely depending upon the protocol to be used, the number of different probes employed in the same assay, whether a single or plurality of lanes are used in the electrophoresis, the availability of excitation and detection devices, and the like. For the most part, the fluorescent moieties that are employed as ligands will absorb in the ultraviolet, infrared, and/or most preferably in the visible range and emit in the ultraviolet, infrared, and/or most preferably in the visible range. Absorption will generally be in the range of about 250 to 750 nm and emission will generally be in the range of about 350 to 800 nm. Illustrative fluorescent moieties include xanthene dyes, naphthylamine dyes, coumarins, cyanine dyes and metal chelate dyes, such as fluorescein, rhodamine, rosamine, the BODIPY dyes (FL, TMR, and TR), dansyl, lanthanide cryptates, erbium. terbium and ruthenium chelates, e.g. squarates, and the like. Additionally, in certain embodiments, one or more fluorescent moieties can be energy transfer dyes such as those described in Waggoner et al., U.S. Pat. No. 6,008,373. The literature amply describes methods for linking fluorescent moieties through a wide variety of linker moieties to other groups. The fluorescent moieties that find use will normally be under 2 kDal, usually under 1 kDal.

Preferred fluorescent moieties can include elaborated conjugated pyran molecules, including xanthenes. Such molecules include eosin, erythrosin, fluorescein, Oregon green, and various commercially available Alexa Fluor® dyes (Molecular Probes, Inc.). Structural examples of such dyes include:

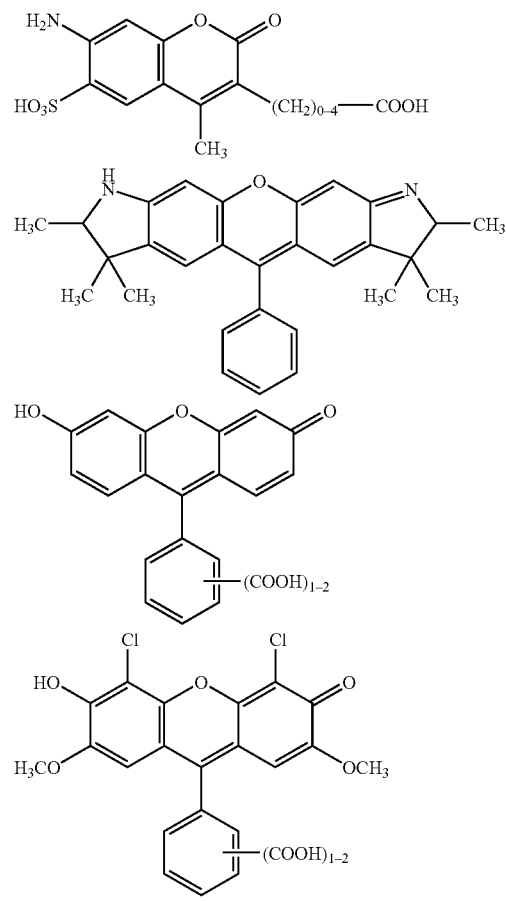

Particularly preferred fluorescent moieties are the rhodamine dyes. These molecules typically have the general structure:

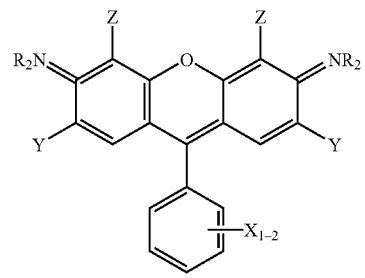

Where X is —CO$_2$H, or —SO$_3$H; Y is —H, —CH$_3$, or together with R forms a six-membered ring; Z is —H or together with R forms a six-membered ring; and R is —H, —CH$_3$, —CH$_2$CH$_3$, or together with Y or Z forms a six-membered ring. Rhodamine molecules such as tetramethylrhodamine, 5-carboxytetramethylrhodamine, 6-carboxytetramethylrhodamine, carboxyrhodamine-6G, rhodamine-B sulfonyl chloride, rhodamine-red-X, and carboxy-X-rhodamine are well known to those of skill in the art. See, e.g., Handbook of Fluorescent Probes and Research Products, Molecular Probes, Inc., 2001, which is hereby incorporated by reference in its entirety. Advantageous properties of rhodamines include high quantum yields, low sensitivity of fluorescence over a pH range of from about pH 3 to about pH 8, advantageous water solubility, good photostability, and absorption of light in the visible spectrum. Particularly preferred fluorescers are 5-carboxytetramethylrhodamine and 6-carboxytetramethylrhodamine.

Other preferred fluorescent moieties include the BODIPY dyes, which are elaborations of a 4-bora-3a,4a-diaza-s-indacene structure. Exemplary structures are provided below:

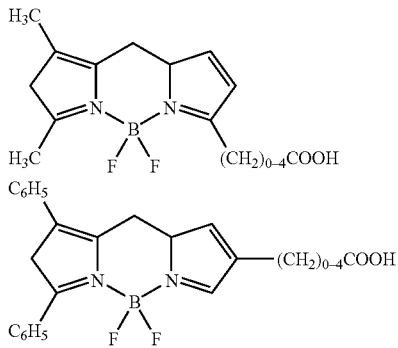

Yet other preferred fluorescent moieties include the cyanine dyes, conjugated structures comprising a polymethine chain terminating in nitrogen atoms. Typically, the nitrogens are themselves part of a conjugated heterocycle. An exemplary structures is provided below:

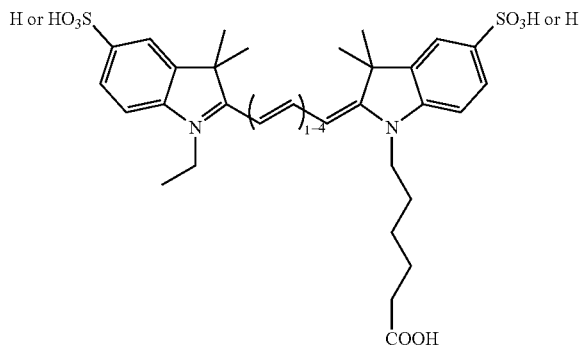

Also of interest for use as ligands are matched dyes as described in U.S. Pat. No. 6,127,134, which is hereby incorporated by reference in its entirety, including all tables, figures, and claims, which is concerned with labeling proteins with dyes that have different emissions, but have little or no effect on relative migration of labeled proteins in an electrophoretic separation. Of particular interest are the cyanine dyes disclosed therein, being selected in '134 because of their positive charge, which matches the lysine to which the cyanine dyes bind. In addition there is the opportunity to vary the polyene spacer between cyclic ends, while keeping the molecular weight about the same with the introduction of an alkyl group in the shorter polyene chain dye to offset the longer polyene. Also described are the BODIPY dyes, which lack a charge. The advantage of having two dyes that similarly affect the migration of the protein would be present when comparing the native and inactived samples, although this would require that in the inactivated sample at least a portion of the protein is monosubstituted.

In each of the foregoing examples of preferred fluorescent moieties, carboxyl groups can provide convenient attachment sites for linker moieties. In the particularly preferred 5- and 6-carboxyrhodamine molecules, the 5- or 6-carboxyl is particularly preferred as an attachment site:

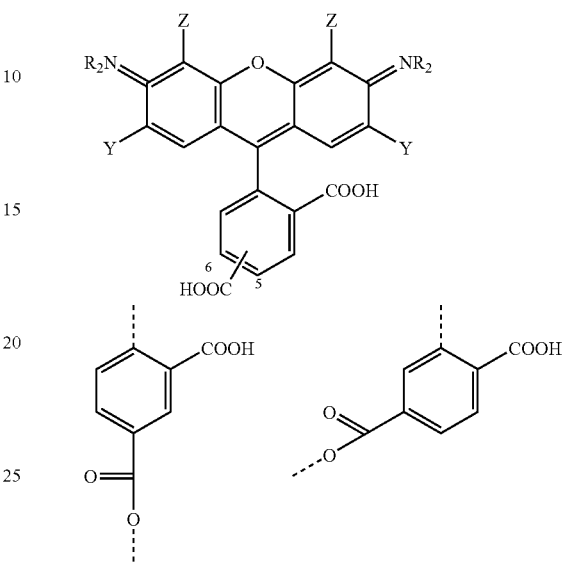

In general, any affinity label-capture reagent commonly used for affinity enrichment, which meets the suitability criteria discussed above, can be used in the method of the invention. Biotin and biotin-based affinity tags are particularly illustrated herein. Of particular interest are structurally modified biotins, such as deiminobiotin or dethiobiotin, which will elute from avidin or streptavidin (strept/avidin) columns with biotin or under solvent conditions compatible with ESI-MS analysis, such as dilute acids containing 10–20% organic solvent. For example, deiminobiotin tagged compounds will elute in solvents below about pH 4.

Design of ABPs and Libraries of ABPs

ABPs may be designed and synthesized using combinatorial chemistry and/or rational design methods. A detailed description of an ABP design strategy, in which a fluorescent moiety can act as a ligand, is provided in PCT Application No. PCT/US02/03808, WO 02/063271, entitled "Activity Based Probe Analysis", filed Feb. 5, 2002, PCT Application No. PCT/US00/34187, WO 01/77684, entitled "Proteomic Analysis," and PCT Application No. PCT/US00/34167, WO 01/77668, entitled "Proteomic Analysis," each of which is hereby incorporated by reference in its entirety, including all tables, figures, and claims. As described therein, goals of a design strategy are to provide ABPs that are able to react covalently with a targeted group of active proteins, while minimizing non-specific labeling.

One strategy that may be utilized to design ABPs is to first identify a potentially reactive amino acid that is conserved at the sequence level in the region that is targeted for ABP labeling, and to select an appropriate functional group for attachment to an appropriate affinity moiety (e.g., an adenosine analogue for ATP binding proteins). Potential reactive amino acids include serine, threonine, tyrosine, lysine, arginine, aspartic acid, glutamic acid, asparagine, glutamine, methionine, and cysteine. One can also consider the composition of the linker moiety between the warhead moiety and the ligand of the ABP, as this can affect the selectivity and specificity of the resulting ABPs. Linker moieties may be either obtained commercially (see, e.g., Pierce Chemical Company Catalog and Handbook 1994–95, pages O-90 through O-110, which is hereby incorporated by reference) or synthesized as needed. A library of molecules comprising, for example, linker chemistries exhibiting varying lengths, hydrophobicities, etc., may be constructed. Moreover, the library of ABPs can also be expanded by varying identity of the ligand (e.g., using a variety of different fluorescent moieties), and/or the location of linker moiety attachment point on the ligand (e.g., 5-TMR linkage vs. 6-TMR linkage), as these can also affect the selectivity and specificity of the resulting ABPs.

In the case of a combinatorial library, as indicated above, numerous variations as to the structure of the ABP can be prepared. These various members may then be screened with a complex protein mixture to determine which members of the library are inactive with inactivated target protein(s), but react with active target protein(s). In carrying out the subject methodology, one or a plurality of ABPs may be added to a complex protein sample as described herein.

In an alternative design strategy, a functional group may be selected that imparts an element of "chemical specificity" to the ABP. In these embodiments, the requirement for an affinity moiety to achieve adequate probe selectivity can be eliminated. The incorporation of an affinity moiety into an ABP can affect the number of proteins targeted by a probe. Thus, depending on the number of target proteins of interest and the similarity of active site binding selectivity, the artisan can choose to include the affinity moiety or not, as required. For example, a fluorophosphonate reactive group provides a classical affinity label for serine hydrolases that selectively reacts with the activated serine nucleophile of catalytic triad and other serine hydrolase classes.

While the number of ABPs that can be used is theoretically unlimited, preferably not more than about 20 are used. Since the sources of the protein mixture will vary widely and one biomolecule may have an influence on the activity of the ABP, as well as on the reactivity of a protein, the mixture may be subject to dilution, fractionation, precipitation, extraction, dialysis, chromatography or other processing to obtain the desired composition. For the most part, the composition will not be significantly modified, maintaining substantially the composition obtained from the source. In some instances the pH may be modified, solvents added, or the like, to enhance the reaction of the active target proteins with the ABP(s) or change the ABP profile as to the active target proteins.

Analysis of Complex Protein Mixtures

The methods of the present invention can be divided generally into two classes, referred to herein for convenience as "screening" methods and "identification" methods.

"Screening" refers to methods in which one or more complex protein mixtures suspected of containing one or more target proteins are mixed with one or more ABPs, whereby active target proteins present in the complex protein mixture(s) are labeled. The proteins are subsequently digested using one or more proteases to generate ABP-labeled peptides. The ABPs of the present invention preferably react with and bind to a single residue on an active target protein, and preferably a single ABP-labeled peptide is generated from each labeled active target protein. A signal is then generated from the ABP-labeled peptide(s), which can be correlated to the presence or amount of labeled active target proteins in the original complex protein mixture, preferably following a separation method (e.g., slab gel or capillary electrophoresis, or liquid chromatography). In these methods, a capture (or sequestration) step (as described hereinafter) is optional.

In contrast, "identification" refers to methods in which the molecular weight and/or the sequence of one or more ABP-labeled peptides, generated as described in the preceding paragraph, are determined by mass spectroscopy ("MS"). In these methods, a capture (sequestration) step is typically performed to purify ABP-labeled peptide(s) prior to MS analysis.

The terms "mass spectrometry" or "MS" as used herein refer to methods of filtering, detecting, and measuring ions based on their mass-to-charge ratio, or "m/z." In general, one or more molecules of interest are ionized, and the ions are subsequently introduced into a mass spectrographic instrument where, due to a combination of magnetic and electric fields, the ions follow a path in space that is dependent upon mass ("m") and charge ("z"). See, e.g., U.S. Pat. No. 6,204,500, entitled "Mass Spectrometry From Surfaces;" U.S. Pat. No. 6,107,623, entitled "Methods and Apparatus for Tandem Mass Spectrometry;" U.S. Pat. No. 6,268,144, entitled "DNA Diagnostics Based On Mass Spectrometry;" U.S. Pat. No. 6,124,137, entitled "Surface-Enhanced Photolabile Attachment And Release For Desorption And Detection Of Analytes;" Wright et al., "Proteinchip surface enhanced laser desorption/ionization (SELDI) mass spectrometry: a novel protein biochip technology for detection of prostate cancer biomarkers in complex protein mixtures," *Prostate Cancer and Prostatic Diseases* 2: 264–76 (1999); and Merchant and Weinberger, "Recent advancements in surface-enhanced laser desorption/ionization-time of flight-mass spectrometry," *Electrophoresis* 21: 1164–67 (2000), each of which is hereby incorporated by reference in its entirety, including all tables, figures, and claims. Molecules (e.g., peptides) in a test sample can be ionized by any method known to the skilled artisan. These methods include, but are not limited to, electron ionization, chemical ionization, fast atom bombardment, field desorption, and matrix-assisted laser desorption ionization ("MALDI"), surface enhanced laser desorption ionization ("SELDI"), photon ionization, electrospray, and inductively coupled plasma.

Figure 2:
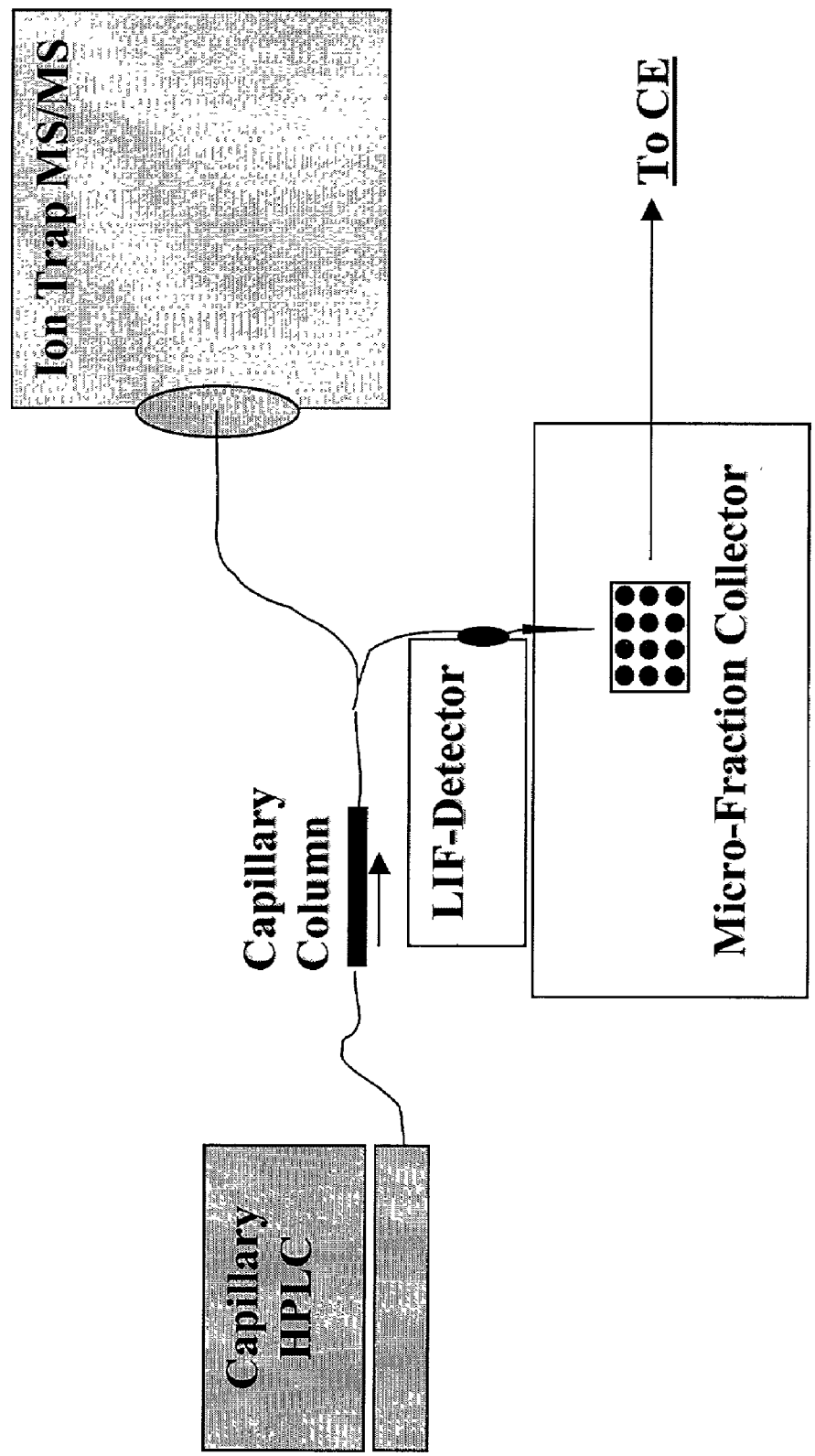
FIG. 2 is a schematic drawing of a typical separation instrument for use in screening and/or identification methods of the present invention.

As used herein, reference to a "screening" method is not intended to imply that a given peptide, and its source protein, cannot be identified in such methods. For example, a particular peptide may exhibit a characteristic migration rate in a separation method that can be used to identify the peptide. Alternatively, several separation methods and/or conditions may be employed, and the separation profile of migration patterns generated for a given peptide can be used to identify the peptide. Instead, the distinction between a screening method and an identification method is the use of MS to directly measure molecular weight in identification methods. Additionally, the skilled artisan will understand that a single complex protein mixture may be analyzed by both screening and identification methods, as exemplified in FIG. 2.

The terms "separation" and "separating" as used herein refer to methods that enrich the concentration of a molecule of interest in a particular location or container relative to other molecules originally present. For example, gel electrophoresis enriches the concentration of molecules that migrate at a particular rate relative to other molecules originally present that migrate at different rates. Numerous additional analytical procedures are known to the artisan for separating and analyzing complex protein mixtures (e.g., chromatographic methods such as HPLC, FPLC, ion exchange, size exclusion; mass spectrometry; differential centrifugation). The term separating does not indicate that a desired component is obtained in a "pure" form; only that the desired component has increased in abundance relative to the other components present. For example, a complex protein mixture may be separated by electrophoresis, whereby a desired component is separated into one or more bands or spots present on a gel. Other, undesired, components may be present in the same band or spot; nonetheless, the desired component will have increased in abundance in that band or spot. A separation profile obtained from a separation procedure can be expressed as an elution time or retention time using a chromatography column, a migration distance, Rf, migration time, or elution time using an electophoresis apparatus, or any other expression commonly used by one of skill in the art to distinguish between separated components.

A particular type of separating method is referred to herein as "capture" or "sequestration." These methods enrich the concentration of molecules capable of being sequestered (e.g., by binding to one or more receptors) relative to other molecules not so capable (e.g., removed by washing out molecules that do not bind to a receptor). In preferred embodiments, one or more molecules are sequestered by being bound to a receptor that is itself bound to a surface. Following removal of unbound molecules, the sequestered molecules may be released from the receptor(s) for further processing. As used herein with respect to receptors, the phrases "specifically binds" and "specific binding" refers to a molecule or molecular complex (e.g., an antibody or binding fragment thereof) that binds to its intended ligand(s) (e.g., a cognate antigen) with at least a 2-fold greater affinity compared to the binding of the receptor to molecules other than the intended ligand(s). In preferred embodiments, such a receptor binds to binding partners with at least a 5-fold, more preferably at least a 10-fold, even more preferably at least a 100-fold, and most preferably at least a 1000-fold greater affinity compared to non-partner binding. In addition to antibody-antigen pairs, suitable receptor-ligand pairs include but are not limited to receptor-hormone pairs, avidin-biotin pairs, streptavidin-biotin pairs, and metal-chelate pairs.

Labeling of Active Target Proteins by ABPs

In carrying out both screening and identification methods, one or a plurality of ABPs will be added to a complex protein mixture as described herein, where the ABPs will react with the active target proteins present. The complex protein mixtures may come from different sources and be used for different purposes. This may include a relatively pure sample of the enzyme to determine the activity in relation to total protein of the sample. The sample may be a single cell or a mixture of cells, a neoplastic sample or other biopsy or tissue comprising a single cell type or a mixture of cell types, such as tissue from an organ, e.g. heart, lung, esophagus, kidney, brain, blood, etc., diseased tissue or healthy tissue, etc. The cells may be prokaryotic or eukaryotic, vertebrate or non-vertebrate, particularly mammalian and more particularly human. The cells or tissues, or lysates thereof, may be prepared in a variety of ways, including fractionation, using chromatography, centrifugation, precipitation, fractionation, fluorescence activated cell sorting, dilution, dialysis, concentration, etc. The sample will usually be treated so as to preserve the activity of the target protein(s), so that the manner of treatment will be mild, ambient or lower temperatures will be used, particularly below 37° C., and other denaturing conditions will be avoided, such as organic solvents, detergents or high salts.

Generally, the amount of each ABP will be sufficient to react with all of the active target protein for the ABP expected to be in the proteome. Typically the amount of each ABP is present in excess over its target proteins on a molar basis. After incubating the reaction mixture, generally for a time for the reaction to go substantially to completion, usually not more than about 2 h, generally for about 0.1–60 min, at a temperature in the range of about 20–40° C., the reaction may be quenched. Since the extent of the reaction will increase with time, the longer the time, the more cross-reactivity may be anticipated. A preferred time will be employed to provide the most favorable results, that is, the greatest level of reaction with the target proteins with the least cross-reactivity.

To enhance the accuracy of the quantitation, internal standards can be employed, where known proteins are reacted with one or more ABPs to provide one or more conjugates of known composition. These internal standards can be used to account for sample losses during processing, account for variations in protein digest efficiencies, and/or account for variations in relative migration times in separation procedures. A predetermined amount of these ABP-labeled standards may be added to a sample, so that the sample will have a known concentration of the standard. The internal standard is then subjected to the same processes as the component of the sample.

Where the procedure is substantially reproducible, an internal standard may be a protein that is also present in the sample being analyzed. One would expect to obtain a predictable signal from the standard, and any increase over this amount can be attributed to active target protein present in the sample. Alternatively, the internal standard may be selected to be different from any conjugate in the sample. In particularly preferred embodiments, one or more internal standards can employ ligands (e.g., fluorescent moieties) that are differentially detectable in comparison to those used for labeling the complex protein mixture. This can be particularly advantageous in separation methods, such as electrophoresis or chromatography, as standard signals can be easily distinguished from signals obtained from the labeled active target proteins.

One or more internal standards may also be selected that provide, for example, a proteolysis site known to react slowly with the protease(s) being employed, and preferably selected to react more slowly than one or more proteins of interest present in the complex protein mixture. Such standards can be used to monitor the course of hydrolysis.

Digesting Labeled Active Target Proteins

Following ABP labeling of active target proteins, both screening and identification methods utilize protein digestion to produce ABP-labeled peptides. The digestion may be performed while the proteins are in solution or when the conjugates are sequestered, e.g., by receptors bound to a solid support. Digestion preferably employs only one protease; however, two or more, usually not more than three, proteases may be used. The proteases may be in solution or bound to a surface. The proteases may be combined in the same reaction mixture, or the sample may be divided into aliquots and each of the aliquots treated with a different protease. Digestion may also occur before binding to the conjugate to a support and/or a after the conjugates are bound to a solid support. Enzymes that find use include, but are not limited to, trypsin, chymotrypsin, bromelain, papain, carboxypeptidase A, B and Y, proteinase A and K, chymopapain, plasmin, subtilisin, clostripain etc.

In particularly preferred embodiments, additional steps can be used to reduce the complexity of the analysis to be performed. For example, the complex protein mixture can be denatured following labeling, e.g., by the addition of urea, guanidinium salts, detergents, organic solvents, etc., in order to reduce or eliminate unwanted proteolysis from endogenous proteases present in the mixture. Additionally, cysteine residues can be reduced and alkylated to maintain the homogeneity of cysteine-containing peptides and to prevent refolding of endogenous proteases following removal of the denaturant. Moreover, proteases can be combined with additional enzymes, such as glycosidases, phosphatases, sulfatases, etc., that can act to remove post-translational modifications from proteins. Examples of such post-translational modifications include, but are not limited to, glycosylations, phosphorylations, sulfations, prenylations, methylations, amidations, and myristolations. Such steps can be mixed and matched by the skilled artisan, depending on the requirements of a particular analysis.

Prior to digestion, a buffer exchange step may be employed, e.g., by gel filtration, dialysis, etc. This step may be used to remove excess ABPs, to remove denaturant, and/or to provide suitable buffer conditions for digestion. In particularly preferred embodiments, buffer exchange is performed by gravity flow gel filtration.

Digestion will be carried out in an aqueous buffered medium, generally at a pH in the range of about 4 to 10, depending on the requirements of the protease. The concentration of the protease will generally be in the range of about $6 \times 1^{-8}$ M to about $6 \times 10^{-6}$ M, more preferably in the range of about $1.8 \times 10^{-8}$ M to about $2 \times 10^{-7}$ M, and most preferably about $6 \times 10^{-7}$ M (e.g., 150 ng/10 µL). The term "about" in this context means +/−10% of a givem measurement. The time for the digestion will be sufficient to go to at least substantial completion, so that at least substantially all of the protein will have been digested. Digests may be performed at a temperature that is compatible with the protease(s) employed, preferably from 20° C. to 40° C., most preferably about 37° C. Where the digestion takes place in solution, the protease may be quenched by any convenient means, including heating or acidification of the sample. Alternatively, quenching can be achieved by sequestering the fragment conjugates with a receptor for the ligand bound to a surface, or by addition of a protease inhibitor (e.g., E64, DIFP, PMSF, etc.). Where the proteins are bound to a surface, the proteases may be washed away before the bound digested protein is released.

Sequestration of ABP-labeled Peptides

It is at this point that screening methods and identification methods typically diverge. Following protein digestion, ABP-labeled peptides can be sequestered, e.g., by binding to receptors for the ligand of one or more ABP(s) employed during the labeling step. This sequestration step is typically not employed in screening methods, as subsequent separation steps (e.g., electrophoresis, chromatography) and detection steps (e.g., generation of fluorescence from fluorescent ABPs) employed in screening methods are often sufficient to distinguish the various ABP-labeled peptides (sequestration may be employed in screening methods when advantageous, such as when a sample is very dilute and sequestration can be used to concentrate ABP-labeled peptides). In contrast, such sequestration step(s) are typically employed in identification methods in order to reduce the number of peptides injected into the MS instrument, thereby simplifying MS analysis.

Preferably, sequestration relies on receptors bound to a solid support that can be easily manipulated during wash steps. The support may be beads, including paramagnetic beads, prepared from various materials, such as Bioglas, polystyrene, polyacrylate, polymethylmethacrylate, polyethylene, polysaccharides, such as Agarose, cellulose, amylose, etc., polyurethane, and the like. Desirably, the support surface will not interfere with the binding of ligand to its cognate receptor, and the receptor may be linked to the support by a hydrophilic bridge that allows for the receptor to be removed from the surface. When beads are employed, the beads will generally have a cross-dimension in the range of about 5 to 100µ. Instead of beads, one may use solid supports, such as slides, the walls of vessels, e.g. microtiter well walls, capillaries, etc. There is an extensive literature of receptor bound supports that is readily applicable to this invention, since the sequestering step is conventional. The sample is contacted with the support for sufficient time, usually about 5 to 60 min, to allow all of the conjugate to become bound to the surface. At this time, all of the non-specifically bound components from the sample may be washed away, greatly enriching the target proteins as compared to the rest of the sample.

Following separation by sequestration, ABP-labeled peptides may then be released from the receptor. The particular method of release will depend upon the ligand-receptor pair. In some instances, one may use an analog of the ligand as a "releasing agent" to release the conjugate. This is illustrated by the use of deimino- or dethiobiotin as the ligand and biotin as the releasing agent. Where this is not convenient, as in the case of many fluorescent moieties as ligands where there may not be a convenient analog, conditions such as high salt concentrations, chaeotropic agents (e.g., isothiocyanate or urea) low pH, detergents, organic solvents, etc., may be used to effect release. Once the conjugate has been released, dialysis, ion exchange resins, precipitation, or the like may be used to prepare the conjugate solution for the next stage.

"Screening" Analysis Methods

In screening methods, a signal is then generated from the various ABP-labeled peptides obtained from the original complex protein mixture. If only a single ABP-labeled peptide is associated with a particular signal (e.g., if each ABP reacts with a single target protein and each ABP is distinguishable) a signal may be generated without further separation. More typically, however, one or more separation methods are employed to separate various ABP-labeled peptides prior to signal generation.

These separation methods include, but are not limited to, liquid chromatography, particularly reverse phase liquid chromatography, where the components are separated by their differences in hydrophobicity, or electrophoresis, particularly slab gel or capillary electrophoresis. The electrophoresis may involve one- or two-dimensional electrophoresis, may be in a gel, may use a capillary or may use a channel in a microfluidic device. See e.g., Opiteck, et al., Anal. Chem. (1998) 258:349–61; U.S. Pat. Nos. 4,415,655; 4,481, 094; 4,865,707; and 4,946,794; Laemmli, U K, Nature (1970) 227, 680–685; and Sambrook, J.; MacCallum, P. & Russell, D. (2001) "Molecular Cloning: A Laboratory Manual." $3^{rd}$ Edition, Cold Spring Harbor Press, Cold Spring Harbor, N.Y. Liquid chromatography may use a combination of size exclusion liquid chromatography followed by RP-HPLC or only RP-HPLC. The conditions employed are conventional for liquid chromatographic separation of proteins and peptides and commercial equipment and materials are available. See, e.g., U.S. Pat. Nos. 5,041, 538 and 5,290,920 and WO91/15228, as exemplary. A suitable eluant can include a water/acetonitrile gradient, optionally containing 0.1% trifluoroacetic acid; 0.1% trifluoroacetic acid; or 0.1% formic acid. The conjugates can be monitored by their fluorescence and may be isolated in wells for further investigation. A separation profile in such methods may be sufficient information to identify the peptide and, therefore, the protein.

For screening, a particularly preferred separation/signal generation method is capillary electrophoresis with laser-induced fluorescence ("CE-LIF"). Capillary electrophoresis methods are well known to the skilled artisan. See, e.g., Kasicka, "Recent advances in capillary electrophoresis of Peptides," *Electrophoresis* (2001) 22:4139–62; Sanchez and Smith, "Capillary electrophoresis," *Methods Enzymol.* (1997) 289:469–78; Xu, "Capillary electrophoresis," *Anal. Chem.* (1995) 67(12):463R-473R; Landers, James (Ed.) Handbook of Capillary Electrophoresis, 2nd Ed. CRC Press, 1997. The resolution of CE peptide separations can be up to 10-fold higher in comparison to reverse phase HPLC, and single molecule detection can be achieved when coupled to LIF. Additionally, multichannel detectors and multicapillary (e.g., 96 capillary) instruments permit multiplexed, high throughput analyses. An exemplary configuration of a CE-LIF multichannel detection instrument is shown in FIG. 1.

A signal can then be generated from the ABP-labeled peptide(s) present, and, if appropriate, the intensity compared from two or more samples. Detection and measurement can be achieved with a CCD, photomultiplier, etc., where the information may be transferred to a data processor for analysis. The different components of the samples and their relative amounts as measured by the intensity of their emissions can be analyzed by the data processor and a profile obtained that compares the number of components and the ratios between two or more samples, and/or results can be compared to other profiles for comparison. In this way, one obtains the characteristics of the complex protein mixture as it is affected by changes in the cells due to differentiation, maturation, cell type and changes in the cellular environment.

"Identification" Analysis Methods

As discussed above, where the migration rates in the separation stages of a screening method provide the necessary identification of the ABP-labeled peptide(s) and, therefore, the protein, and provide quantitation of the protein, no further analysis is required. However, where further confirmation of the results from the earlier analysis is desired or the earlier results do not provide certainty as to the identification and amount of a particular component, an identification method using mass spectrometry (MS) can be employed. See, for example, WO 00/11208. The use of mass spectrometry will be described below. Such identification methods potentially provide greater information, but requires greater sample size in comparison to, for example, capillary electrohoresis, and has a lower throughput.

In identification methods, chromatographic and/or electrophoretic separation methods as described herein may be used to simplify the mixtures introduced into the mass spectrometer, allowing for a more accurate analysis. These separation methods may be employed prior to, following, or in lieu of sequestration of the ABP-labeled peptides described above. The use of fluorescent moieties as ABP ligands can permit the use of an online fluorescence detector to trigger ESI-MS data collection or fraction collection for subsequent analysis, e.g., providing sample on a MALDI plate. In this way, only fractions and bands that contain ABP-labeled peptides will be selected for further processing, thereby avoiding using the MS with certain fractions.

In particularly preferred embodiments, the identification methods described herein can be combined with one or more separation methods to develop a "separation profile" that can be used to identify ABP-labeled peptides without the need for MS analysis. In these methods, a sample (e.g., material from a chromatography column) is divided into at least two portions; one portion is used for MS analysis, and the other portion(s) are used for one or more separation methods (e.g., a single CE run, or two or more CE runs using different separation conditions). The peptide identification obtained from the MS analysis can be assigned to the observed separation profile (e.g., the elution time of the peptide observed in the CE run(s)). Observation of this separation profile in subsequent samples can then be correlated to the peptide known to exhibit that separation profile.

The identification methods described herein may also utilize ABPs that differ isotopically in order to enhance the information obtained from MS procedures. For example, using automated multistage MS, the mass spectrometer may be operated in a dual mode in which it alternates in successive scans between measuring the relative quantities of peptides obtained from the prior fractionation and recording the sequence information of the peptides. Peptides may be quantified by measuring in the MS mode the relative signal intensities for pairs of peptide ions of identical sequence that are tagged with the isotopically light or heavy forms of the reagent, respectively, and which therefore differ in mass by the mass differential encoded with the ABP. Peptide sequence information may be automatically generated by selecting peptide ions of a particular mass-to-charge (m/z) ratio for collision-induced dissociation (CID) in the mass spectrometer operating in the $MS^n$ mode. (Link, et al., (1997) Electrophoresis 18:1314–34; Gygi, et al., (1999) idid 20:310–9; and Gygi et al., (1999) Mol. Cell. Biol. 19:1720–30). The resulting CID spectra may be then automatically correlated with sequence databases to identify the protein from which the sequenced peptide originated. Combination of the results generated by MS and $MS^n$ analyses of affinity tagged and differentially labeled peptide samples allows the determination of the relative quantities as well as the sequence identities of the components of protein mixtures.

Protein identification by $MS^n$ may be accomplished by correlating the sequence contained in the CID mass spectrum with one or more sequence databases, e.g., using computer searching algorithms (Eng. et al. (1994) J. Am. Soc. Mass Spectrom. 5:976–89; Mann, et al., (1994) Anal. Chem. 66:4390–99; Qin, et al., (1997) ibid 69:3995–4001; Clauser, et al., (1995) Proc. Natl. Acad. Sci. USA 92:5072–76). Pairs of identical peptides tagged with the light and heavy affinity tagged reagents, respectively (or in analysis of more than two samples, sets of identical tagged peptides in which each set member is differentially isotopically labeled) are chemically identical and therefore serve as mutual internal standards for accurate quantitation. The MS measurement readily differentiates between peptides originating from different samples, representing different cell states or other parameter, because of the difference between isotopically distinct reagents attached to the peptides. The ratios between the intensities of the differing weight components of these pairs or sets of peaks provide an accurate measure of the relative abundance of the peptides and the correlative proteins because the MS intensity response to a given peptide is independent of the isotopic composition of the reagents. The use of isotopically labeled internal standards is standard practice in quantitative mass spectrometry (De Leenheer, et al., (1992) Mass Spectrom. Rev. 11:249–307).

The ABP-labeled peptides may provide specific fragmentation patterns in MS procedures. In this manner, the fragmentation pattern of the ABP-labeled peptides will aid in the identification of the proteins, or identifying which peptide(s) from a protein are labeled by an ABP. As an added advantage, where the ABP is positively charged, it will enhance the signal due to its easier ionization.

Isotopically distinguishable ABPs are useful when using MS detection for either the second dimension of separation, as in MALDI/TOF or when doing identification as in MS$^n$. Convenient isotopic labels are $^2$H, $^{13}$C, $^{15}$N, $^{17}$O, $^{18}$O or $^{34}$S. The use of the isotopically labeled ABPs also allows for the use of isotopically differing internal standards. The internal standard ABP will typically be otherwise identical to the sample ABP.

The above procedures allow for analysis of complex protein mixtures such as proteomes. The analysis can be associated with screening of candidate compounds to determine the effect of the compound on the regulation of the target proteins, identification of the pathways that the candidate compound affects and the cellular response to the candidate compound. In this way the effectiveness of drugs may be analyzed, cross-reactivity determined, toxicity evaluated and other effects on cell physiology determined. Besides candidate compounds, the subject analysis may be used with natural products, environmental sample screening, and the like. In each case one can identify specific proteins that are affected by the environment of the cells and compare the effect of the environment with changes observed with other environments. The subject methods can be used in high throughput primary or secondary screening, where candidate compounds are evaluated for their efficacy and cross-reactivity, their influence on physiologic pathways and their interactions with other drugs that may be taken for the same indication.

Kits can be provided that combine one or more ABPs for specific and/or related groups of proteins, with the proteolytic enzymes, in solution, but usually either as a lyophilized or bound to a support. Also included can be solid supports for the sequestration of the conjugates, both intact and fragment, where the supports may be any solid support, such as particles and beads of from about 5 to 100μ, the walls of vessels, such as the microtiter wells of microtiter plates, capillaries, etc., to which the receptor is bound. The solid supports may be treated with an innocuous protein, such as serum albumin, to occupy hot spots and inhibit non-specific binding. Pre-labeled internal standards may also be supplied.

The following examples are offered by way of illustration and not by way of limitation.

EXAMPLE 1

Preparation of FP-PEG-TMR (fluorophosphonate-tetraethyleneglycol-tetramethylrhodamine)

Compound 1a is the starting material tetraethyleneoxy (3,6,9-oxa-1,11-diolundecane) and compound 1b is the starting material decylene-1,10-diol as depicted in the flow chart in FIG. 1.

Compound 2. A solution of 1 (3.9 g, 20.0 mmol, 3.0 equiv) in DMF (8.0 mL) was treated with TBDMSCl (1.0 g, 6.64 mmol, 1.0 equiv) and imidazole (0.9 g, 13.3 mmol, 2.0 equiv) and the reaction mixture was stirred for 12 h at room temperature. The reaction mixture was then quenched with saturated aqueous NaHCO3 and partitioned between ethyl acetate (200 mL) and water (200 mL). The organic layer was washed with dried (Na2SO4) and concentrated under reduced pressure. Chromatography (SiO2, 5×15 cm, 50–100% ethyl acetate-hexanes) afforded 2 (1.1 g, 2.0 g theoretical, 55%) as a colorless oil: 1H NMR (CDCl3, 400 MHz) δ 3.8–3.5 (m, 16H, CH2OR), 0.88 (s, 9H, CH3C), 0.0 (s, 6H, CH3Si).

Compound 3. A solution of 2 (0.61 g, 2.0 mmol, 1.0 equiv) in benzene (15 mL, 0.13 M) was treated sequentially with PPh3 (2.6 g, 10.0 mmol, 5 equiv), 12 (2.3 g, 9.0 mmol, 4.5 equiv), and imidazole (0.7 g, 10.3 mmol, 5.2 equiv) and the reaction mixture was stirred at room temperature for 30 min, producing a yellow-orange heterogeneous solution. The soluble portion of the reaction mixture was removed and the insoluble portion washed several times with ethyl acetate. The combined reaction and washes were then partitioned between ethyl acetate (200 mL) and saturated aqueous Na2S2O3 (200 mL). The organic layer was washed sequentially with H2O (100 mL) and saturated aqueous NaCl (100 mL), dried (Na2SO4), and concentrated under reduced pressure. Chromatography (SiO2, 5×15 cm, 5–25% ethyl acetate-hexanes) afforded 3 (0.54 g, 0.82 g theoretical, 66%) as a colorless oil: 1H NMR (CDCl3, 400 MHz) δ 3.85–3.60 (m, 12H, CH2OR), 3.54 (t, J=5.6, 2H, CH2OTBDMS), 3.23 (t, J=7.0 Hz, 2H, CH2I), 0.88 (s, 9H, CH3C), 0.0 (s, 6H, CH3Si).

Compound 4. Triethylphosphite (1.2 mL, 7.0 mmol, 5.4 equiv) was added to 3 (0.53 g, 1.29 mmol, 1.0 equiv) and the mixture was stirred at 150° C. for 1 h. The reaction mixture was cooled to room temperature and directly submitted to flash chromatography (SiO2, 5×15 cm, 100% ethyl acetate) to afford 4 (0.43 g, 0.54 g theoretical, 80%) as a colorless oil: 1H NMR (CDCl3, 400 MHz) δ 4.20–4.05 (m, 4H, CH3CH2OP), 3.80–3.55 (m, 14H, CH2O R), 2.15 (m, 2H, CH2P), 1.31 (t, J=6.0 Hz, 6H, CH3CH2OP), 0.88 (s, 9H, CH3C), 0.0 (s, 6H, CH3Si).

Compound 5. A solution of compound 4 (0.21 g, 0.5 mmol, 1.0 equiv) in CH2Cl2 (2.8 mL, 0.18 M) was treated with HF-pyridine (0.084 mL, ~0.84 mmol, ~1.7 equiv). The reaction was stirred at 25° C. for 30 min and then partitioned between ethyl acetate (100 mL) and water (100 mL). The organic layer was dried (Na2SO4) and concentrated under reduced pressure. Chromatography (SiO2, 2×8 cm, 3–10% CH3OH—CH2Cl2) afforded 5 (0.050 g, 0.28 g theoretical, 32.5%) as a clear oil: 1H NMR (CDCl3, 400 MHz) δ 4.20–4.05 (m, 4H, CH3CH2OP), 3.80–3.55 (m, 14H, CH2OR), 2.15 (m, 2H, CH2P), 1.31 (t, J=6.0 Hz, 6H, CH3CH2OP); MALDI-FTMS m/z 337.1377 (C12H27O7P+Na+requires 337.1387).

Compound 6. A solution of 5 (0.030 g, 0.096 mmol, 1.0 equiv) in DMF (0.28 mL, 0.34 M) was treated sequentially with N,N-disuccinimidyl carbonate (0.058 g, 0.22 mmol, 2.2 equiv) and triethylamine (0.035 μL, 0.25 mmol., 2.5 equiv). The reaction mixture was stirred at room temperature for 12 h and then partitioned between CH2Cl2 (100 mL) and H2O(100 mL). The organic layer was washed with saturated aqueous NaCl (100 mL), dried (Na2SO4), and concentrated under reduced pressure. Chromatography (SiO2, 2×8 cm, 1–10% CH3OH—CH2Cl2) afforded 50.035 g, 0.043 g theoretical, 81%) as a clear oil: 1H NMR (CDCl3, 400 MHz) δ 4.45 (m, 2H, CH2OC(O)OR), 4.20–4.05 (m, 4H, CH3CH2OP), 3.80–3.55 (m, 12H, CH2OR), 2.84 (s, 4H, CH2C(O)N), 2.15 (m, 2H, CH2P), 1.31 (t, J=6.0 Hz, 6H, CH3CH2O P). MALDI-FTMS ml/z 478.1456 (C17H30NO11P+Na+requires 478.1449).

Compound 7. A solution of 6 (0.020 g, 0.044 mmol, 1.0 equiv) in CH2Cl2 (0.14 mL, 0.40 M) was cooled to 0° C. and treated with oxalyl chloride (0.082 mL, 2M in CH2Cl2, 0.164 mM 3.7 equiv). The reaction mixture was allowed to warm to room temperature and stirred for 18 h. The reaction mixture was then concentrated under a stream of gaseous nitrogen and the remaining residue treated with H2O (0.1 mL) for 5 min. The H2O was evaporated under a stream of gaseous nitrogen and the remaining residue dried by vacuum to provide 7 (0.015 mg, 0.019 mg theoretical, 80%) as a clear oil/film: 1H NMR (CDCl3, 400 MHz) δ 4.45 (m, 2H, CH2OC(O)OR), 4.10 (m, 2H, CH3CH2OP), 3.80–3.55 (m, 12H, CH2OR), 2.84 (s, 4H, CH2C(O)N), 2.15 (m, 2H, CH2P), 1.31 (t, J=6.0 Hz, 3H, CH3CH2OP).

Compound 8. A solution of 7 (0.007 g, 0.016 mmol, 1.0 equiv) in CH2Cl2 (0.22 mL, 0.075 M) at −78° C. was treated with (diethylamino)sulfur trifluoride (DAST, 0.007 mL, 0.048 mmol, 3.0 equiv) and the reaction mixture was stirred for 10 min. The reaction mixture was then partitioned between ethyl acetate (100 mL) and H2O (100 mL) and the organic layer was washed with saturated aqueous NaCl (100 mL), dried (Na2SO4), and concentrated under reduced pressure. Chromatography (SiO2, Pasteur pipette, 100% ethyl acetate) afforded 8 (0.003 g, 0.007 g theoretical, 42%) as a clear oil: 1H NMR (CDCl3, 400 MHz) δ 4.45 (m, 2H, CH2OC(O)OR), 4.27 (m, 2H, CH3CH2OP), 3.80–3.55 (m, 12H, CH2O R), 2.84 (s, 4H, CH2C(O)N), 2.32–2.26 (m, 2H, CH2P), 1.31 (t, J=6.0 Hz, 3H, CH3CH2OP).

Compound 9. A solution of tetramethylrhodamine ethylenediamine (Molecular Probes, Eugene, Oreg.) (0.005 g, 0.010 mmol, 1.0 equiv) in DMF (0.5 mL, 0.020 M) was added to compound 8 (neat, 0.007 g, 0.016 mmol, 1.7 equiv) and the reaction mixture was stirred for 30 min at room temperature. The solvent was removed under vacuum and the products were resuspended in a 0.35 mL of a water-acetonitrile mixture (1:1 v./v.) containing 0.1% (v./v.) trifluoroacetic acid. An aliquot of this solution (0.30 mL) was injected on a preparative reverse phase HPLC column (Haisil 100 C8, Higgins Analytical, 20 mm×150 mm), separated using a 0–100% acetonitrile gradient in 30 minutes at 10 mL per min. The retention time under these conditions was 19.95 min. The solvent was removed under vacuum using a rotary evaporator, and afforded 9 (0.0035 g, 0.0042 mmol, 42%) as a darkly colored oil.

EXAMPLE 2

Complex Protein Mixture Analysis

General Materials and Methods. Activity based probes were synthesized as described in Example 1. Rat fatty acid amide hydrolase (FAAH) was expressed in *E. coli* and purified using standard protocols. Porcine trypsin and equine butyrylcholinesterase were purchased from Sigma corp. Urokinase plasminogen activator, tissue plasminogen activator, prostate specific antigen, and bovine trypsin were purchased from Calbiochem (San Diego, Calif.).

Labeling of Purified Serine Hydrolases. Each purified serine hydrolase was diluted to 0.01–0.05 mg/mL in reaction buffer (50 mM Tris pH 7.0, 100 mM NaCl) containing 1 mg/mL heat denatured rat liver soluble proteome. The mixtures were labeled for 1 h at 20° C. with 2 µM FP-Peg-TAMRA. Unreacted probe was then removed by gel filtration on 10DG columns (Bio-Rad).

Preparation of Internal Standard Proteins. Bovine trypsin, porcine trypsin, and porcine elastase were diluted to 0.25 mg/mL in reaction buffer and labeled with 20 µM FP-Peg-BodipyFL for 30 min. Excess probe was removed by gel filtration on 10DG columns (Bio-Rad). The proteins were mixed together and $\frac{1}{30}^{th}$ volume of this cocktail was used added to each sample as an internal standard.

Preparation and Digestion of Complex Protein Mixtures. For studies involving purified serine hydrolases, the eight labeled proteins were mixed together and 3 µL of the cocktail was added to 27 µL of either rat liver soluble proteome (1.5 mg/mL protein), rat liver membrane proteome (1.5 mg/mL protein), rat brain soluble proteome (1.5 mg/mL protein), rat brain membrane proteome (1.5 mg/mL protein), MDA-MB-231 conditioned media (0.5 mg/mL protein), MDA-MB-435 conditioned media 0.5 mg/mL protein), whole yeast lysate (8 mg/mL), or human plasma (50 mg/mL protein). FAAH inhibition experiments were conducted by pre-incubating rat brain or testis membrane fractions (1.5 mg/mL protein, in reaction buffer) in the presence or absence of 50 µM oleoyl trifluoromethylketone for 15 min followed by the addition of 5 µM FP-Peg-TAMRA and incubation at 20° C. for 1 h.

Following labeling, the proteomes were denatured by adding 1 volume of 12M urea (prepared at 50° C. to allow for complete dissolution of the urea), and $\frac{1}{100}$ volume of DTT from a fresh 1M stock. The mixture was then heated to 65° C. for 15 min. Iodoacetamide was added to 40 mM from a fresh 1M solution and the solution was incubated at 37° C. for 30 min to alkylate available cysteine residues.

Prior to trypsin digest, the buffer was exchanged by gel filtration to remove excess reagents and unreacted probe, and reduce the urea concentration to a suitable concentration (2M) for trypsin activity. Gel filtration was performed using sephadex G-25 superfine resin (Amersham Biosciences) in custom 96-well filter plates from Innovative Microplate. The custom filter plates were designed to support gravity flow and allow collection volumes as small as 20 µL. Gel filtration was performed with 20 µL or 50 µL of sample using 350 µL or 600 µL of hydrated beads respectively. Each well was rinsed prior to use with 5 bed volumes of digestion buffer (2M urea 10 mM ammonium bicarbonate). Samples were applied to columns, followed by a defined amount of digestion buffer (150 µL for 350 µL columns, 200 µL for 600 µL columns). Three fractions of 20 µL or 50 µL were then collected into 96-well plates. The highest concentration of protein was consistently observed to elute in the second fraction.

Following gel filtration, the samples were treated with 150 ng trypsin (sequencing grade modified trypsin, Promega) per 10 L of sample for 1 h at 37° C. Digests were stopped and prepared for CE by addition of $\frac{1}{20}^{th}$ volume each of 200 mM citrate, and 10% triton X-100.

Capillary Electrophoresis. Capillary electrophoresis was performed using a Beckman PACE MDQ CE system. Excitation was provided by a 100 mW, frequency doubled (532 nm) Nd:YAG laser (Coherent inc.). The laser was mounted on an optical breadboard and focused into one end of a 100 µM fiber optic cable using a laser-fiber coupler (OZ optics). The other end of the fiber optic cable was interfaced with the Beckman CE using an SMA 905 connector. The laser power measured at the capillary launch point was 25 mW. Fluorescence was collected into two channels, one for the TAMRA signal and one for the BodipyFL signal. The TAMRA channel contained a 532 nm notch filter, followed by a 580 nm bandpass filter (Omega Optical). The BodipyFL channel contained a 520 nm short pass filter, followed by a 510 nm bandpass filter.

Samples were separated in 100 µM×60 cm eCAP DNA capillaries (Beckman Coulter inc.). The running buffer contained 50 mM aspartic acid, 10 mM hepes, 0.2% triton X-100 (pH 3.1 without. adjustment). Prior to each run, capillaries were rinsed at 20 psi for 1.5 min. Samples were injected for 6 s at 0.1 psi (20 nL estimated injection volume)

then separated by applying 25 kV (inlet=anode) for 45 minutes. The measured current under these conditions was 23 μA.

Figure 3:
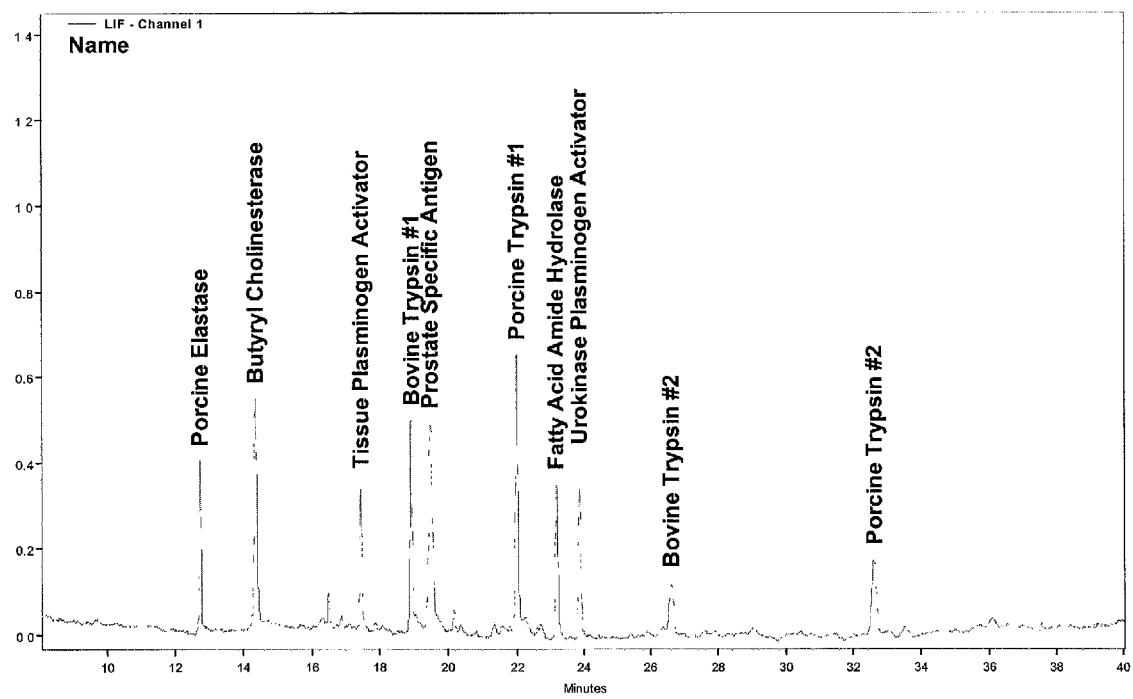
FIG. 3 is a capillary electrophoresis profile for peptides generated from eight serine hydrolases digested in a complex protein mixture (liver cytosol).

The results of a typical analysis are shown in FIG. 3, which displays a capillary electrophoresis profile for peptides generated from eight serine hydrolases digested in a complex protein mixture (liver cytosol). Two different labeled peptides were generated by proteolysis of each of two of these proteins (porcine and bovine trypsin), while single peptides were generated from the remaining six proteins. The reproducibility of these results across several CE procedures is shown in the table below:

| Protein | Migration Time RMSD % | Peak Height RMSD % | Peak Area RMSD % |
|---|---|---|---|
| Elastase | 0.073006 | 15.81026 | 13.90155 |
| Butyrylcholinesterase | 0.019949 | 13.64885 | 15.25825 |
| TPA | 0.098537 | 22.37438 | 21.71691 |
| Bovine trypsin #1 | 0.101285 | 37.06117 | 40.10104 |
| PSA | 0.104278 | 26.65682 | 28.78821 |
| Porcine trypsin #1 | 0.105724 | 41.79855 | 45.2839 |
| FAAH | 0.129092 | 20.59908 | 20.97169 |
| UPA | 0.331954 | 27.00883 | 23.02499 |
| Bovine trypsin #2 | 0.128533 | 40.09026 | 45.68084 |
| Porcine trypsin #2 | 0.090917 | 39.96854 | 40.26177 |

EXAMPLE 2

ABP-Labeled Peptide Identification and CE Migration Determination

A complex protein mixture is labeled with an ABP containing TAMRA as the ligand. The sample is then processed, and digested as in example 1. For peptide identification from a proteome, typically 1–5 mg of total protein is used. Following digestion, $1/10^{th}$ volume of 10% SDS (w/v) is added to the sample and it is heated to 65° C. for 5 min. The sample is then mixed with an equal volume of 2× binding buffer (2% Triton X-100, 1% Tergitol NP40 type, 300 mM NaCl, 2 mM EDTA, 20 mM Tris pH 7.4), before adding 20–100 μL of beads containing anti-TAMRA antibodies. The mixture is rotated at ambient temperature for 1 h. The beads are pelleted by centrifugation and the supernatant removed. The beads are then washed 3 times with 1 mL of 1× binding buffer containing 1% SDS, followed by 3 washes with 50 mM Tris pH 8.0, and 2 washes with deionized water. Captured peptides are eluted from the beads with 2 bead volumes of 50% acetonitrile/$H_2O$+0.5% trifluoroacetic acid. The eluted peptides are concentrated to approximately 10–20 μL before proceeding.

The sample of affinity enriched ABP labeled peptides is injected onto a 300 μM C18 reverse phase HPLC column at a flow rate of 5 μL per minute. Peptides are separated over a 2 h gradient from 5–50% acetonitrile+0.1% formic acid in $H_2O$+0.1% formic acid. The eluant of the HPLC column is split, sending approximately 0.5–1 μL per minute to an ESI-ion trap mass spectrometer, and the other 4–4.5 μL per minute to a capillary fluorescence detector and a fraction collector in series (see FIG. 2). During the run, the mass spectrometer alternates between MS mode and MS/MS mode to obtain all data necessary to identify the proteins giving rise to the observed peptides. Fractions are collected at 0.5 min intervals into a V-bottom 96 well-plate pre-loaded with 10 μL of 50 mM aspartic acid containing internal standard peptides.

Following the run, MS data is searched using a program such as SEQUEST or MASCOT, with the appropriate mass of the ABP tag included in the search. The presence of the ABP tag on each identified peptide can be confirmed by the presence of a fluorescence signal at the appropriate time for each species. Once the species present in the sample are identified, their positions in the 96-well can be determined and these fractions can be run on a CE instrument to determine their migration patterns. Additionally, since the CE uses minimal amounts of sample (20 nL), excess material can be stored for future reference.

The subject methods provide an efficient means for screening cells for their responses to change in status and environment. The methodology allows for substantial simplification of the sample to be analyzed. By using a combination of ABPs and digestion, the resulting fragment conjugates can be more readily analyzed for the proteins present in the proteome. The ABP provides substantial assurance that the conjugate will have a single probe at a single site. Upon digestion this will lead to a single fragment conjugate. The proteolysis will substantially reduce the likelihood of having a glycolytically modified amino acid, particularly having fragments that are differentially glycosylated. In this manner, the number of different fragments associated with the same protein is diminished. There is also less likelihood of other artifacts being introduced that increase the number of fragments resulting from a single protein.

For status, one can determine the regulation of target proteins as cells differentiate, mature or change their characteristics. For environment, one can evaluate candidate drugs in real time, using an automatable system that allows for the direct comparison of a plurality of drugs. The target proteins can be quantitated. Since the target proteins are in their active state, a dynamic picture of the state of the cell is determined. This means that one is obtaining a true picture of how the cell responds to the change in environment and the pathways that are active in the presence of the candidate drug. The subject methods provide for a more accurate and complete understanding of the effect of a drug. By virtue of the methods, one can perform numerous assays with a single drug, varying the cells to obtain a more complete picture of the effect of the drug on a host. By determining a spectrum of effects, a better understanding of the activity of the drugs is obtained.

In addition, the subject methods permit different levels of analysis as to the time required for the determinations. In those cases where quantitation can be achieved from the migration of the conjugate, rapid parallel determinations can be made. Where further analysis is required, the capabilities of mass spectrometry are enlisted, where the presence of a fluorescent marker permits selection of only those fractions or bands that contain components of interest.

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety. In case of conflict, the present specification, including definitions, will control. In addition, the materials, methods, and examples are illustrative only and not intended to be limiting.

While the invention has been described in detail with reference to certain preferred embodiments thereof, it will be understood that modifications and variations are within the spirit and scope of that which is described and claimed.

What is claimed is:

1. A method for determining the presence, amount, or activity of one or more active target proteins in a complex protein mixture, the method consisting of the sequential steps of:
   (a) contacting said complex protein mixture with a single activity based probe that specifically binds predominantly to a single target site on one or more active target proteins;
   (b) optionally removing from said complex protein mixture one or more components of said complex protein mixture not bound to said probe;
   (c) proteolyzing said active target protein(s) to produce a product mixture;
   (d) optionally binding said proteolyzed target protein(s) to a solid support;
   (e) separating said product mixture into two or more components, one or more of which consist essentially of peptides bound to said probe; and thereafter
   (f) generating a signal from said peptides bound to said probe, wherein said signal is correlated to the presence, amount, or activity of said one or more active target proteins in said complex protein mixture.

2. A method according to claim 1, wherein said solid support consists essentially of a receptor that specifically binds to said probe.

3. A method according to claim 2, wherein said probe consists essentially of a functional group, a detectable label, an optional affinity group, and an optional linking group, and said receptor is avidin, streptavidin, or an antibody or fragment thereof that binds to said detectable label.

4. A method according to claim 3, wherein said detectable label consists essentially of a fluorescent moiety, and said signal is a fluorescent signal generated from said probe.

5. A method according to claim 1, wherein said signal is a mass spectrum.

6. A method according to claim 1, wherein, prior to said proteolyzing step (c), one or more components of said complex protein mixture not bound to said probe are removed from said complex protein mixture.

7. A method according to claim 1, wherein said probe consists essentially of a functional group, a detectable label, an optional affinity group, and an optional linking group, and said detectable label is selected from the group consisting of a fluorescent moiety and biotin.

8. A method according to claim 1, wherein said separating step (e) is selected from the group consisting of affinity separation, gel electrophoresis, capillary electrophoresis, liquid chromatography HPLC, electrospray ionization mass spectrometry, MALDI mass spectrometry and combinations thereof.

9. A method according to claim 6, wherein said one or more active target proteins bound to said probe are bound to a solid support, thereby facilitating said removing step (b).

10. A method for determining the presence, amount, or activity of one or more active target proteins in a complex protein mixture, the method consisting of the sequential steps of:
    (a) contacting said complex protein mixture with a single activity based probe that specifically binds predominantly to a single target site on one or more active target proteins;
    (b) optionally adding one or more standard proteins to said complex protein mixture prior to proteolysis step (d), wherein said standard protein(s) are optionally labeled with an activity based probe prior to addition to said complex protein mixture;
    (c) optionally removing from said complex protein mixture one or more components of said complex protein mixture not bound to said probe;
    (d) proteolyzing said active target protein(s) to produce a product mixture;
    (e) optionally binding said proteolyzed target protein(s) to a solid support;
    (f) separating said product mixture into two or more components, one or more of which consist essentially of peptides bound to said probe; and thereafter
    (g) generating a signal from said peptides bound to said probe, wherein said signal is correlated to the presence, amount, or activity of said one or more active target proteins in said complex protein mixture.

11. A method according to claim 10, wherein said standard protein(s) are labeled with an activity based probe prior to addition to said complex protein mixture.

12. A method according to claim 11, wherein said standard protein(s) are labeled with an activity based probe consisting essentially of a functional group, a detectable label, an optional affinity group, and an optional linking group, wherein said detectable label is distinguishable from said activity based probe contacted with complex protein mixture.

13. A method according to claim 1, wherein said complex protein mixture is a proteome.

14. A method for determining the presence, amount, or activity of one or more active target proteins in a complex protein mixture, the method consisting of the sequential steps of:
    (a) contacting said complex protein mixture with a single activity based probe that specifically binds predominantly to a single target site on one or more active target proteins, wherein said probe comprises a fluorescent moiety;
    (b) optionally removing from said complex protein mixture one or more components of said complex protein mixture not bound to said probe;
    (c) proteolyzing said active target protein(s) to produce a product mixture;
    (d) optionally binding said proteolyzed target protein(s) to a solid support consisting essentially of an antibody or fragment thereof that binds to said fluorescent moiety;
    (e) separating said product mixture into two or more components, one or more of which consist essentially of peptides bound to said probe; and thereafter
    (f) generating a signal from said peptides bound to said probe, wherein said signal is correlated to the presence, amount, or activity of said one or more active target proteins in said complex protein mixture.

15. A method according to claim 14, wherein said signal is a fluorescent signal generated from said probe.

16. A method according to claim 14, wherein said signal is a mass spectrum.

17. A method according to claim 14, wherein, prior to said proteolyzing step (c), one or more components of said complex protein mixture not bound to said probe are removed from said complex protein mixture.

18. A method according to claim 14, wherein said probe consists essentially of a functional group, a detectable label, an optional affinity group, and an optional linking group, and said detectable label is selected from the group consisting of a fluorescent moiety and biotin.

19. A method according to claim 14, wherein said separating step (e) comprises one or more separation methods selected from the group consisting of affinity separation, gel electrophoresis, capillary electrophoresis, liquid chromatography, HPLC, electrospray ionization mass spectrometry and MALDI mass spectrometry.

20. A method according to claim 14, wherein prior to said proteolyzing step (c), said one or more active target proteins bound to said probe are bound to a solid support.

21. A method for determining the presence, amount, or activity of one or more active target proteins in a complex protein mixture, the method consisting of the sequential step of:
   (a) contacting said complex protein mixture with a single activity based probe that specifically binds predominantly to a single target site on one or more active target proteins, wherein said probe comprises a fluorescent moiety;
   (b) adding one or more standard proteins to said complex protein mixture, wherein said standard protein(s) are optionally labeled with an activity based probe prior to addition to said complex protein mixture;
   (c) optionally removing from said complex protein mixture one or more components of said complex protein mixture not bound to said probe;
   (d) proteolyzing said active target protein(s) to produce a product mixture;
   (e) optionally binding said proteolyzed target protein(s) to a solid support consisting essentially of an antibody or fragment thereof that binds to said fluorescent moiety;
   (f) separating said product mixture into two or more components, one or more of which consist essentially of peptide bound to said probe; and thereafter
   (e) generating a signal from said peptides bound to said probe, wherein said signal is correlated to the presence, amount, or activity of said one or more active target proteins in said complex protein mixture.

22. A method according to claim 21, wherein said standard protein(s) are labeled with an activity based probe prior to addition to said complex protein mixture.

23. A method according to claim 22, wherein said standard protein(s) are labeled with an activity based probe comprising the fluorescent moiety that is distinguishable from said activity based probe contacted with complex protein mixture.

24. A method according to claim 14, wherein said complex protein mixture is a proteome.

25. A method for comparing the presence, amount or activity of one or more active target proteins in each of two or more discrete proteomes, the method consisting of the sequential steps of:
   (a) contacting each of said discrete proteomes with a single activity based probe that binds predominantly to a single target site on one or more active target proteins, wherein the same activity based probe is used for each discrete proteome;
   (b) optionally removing from each of said discrete proteomes one or more components of said discrete proteome not bound to said probe;
   (c) proteolyzing said discrete proteomes to produce a product mixture;
   (d) optionally binding said proteolyzed target protein(s) to a solid support;
   (e) separating each of said product mixtures into two or more components, one or more of which comprise peptides bound to said probe; and thereafter
   (f) comparing the presence, amount or activity of the active target proteins in each of the discrete proteomes by generating a signal from said one or more components comprising peptides bound to said probe.

26. The method according to claim 25, wherein said activity based probe binds specifically to a single target site on one or more active target proteins.

27. The method according to claim 25, wherein said activity based probe covalently binds to a single target site on one or more active target proteins.

28. A method according to claim 25, wherein said solid support consists essentially of a receptor that specifically binds to said probe.

29. A method according to claim 28, wherein said probe consists of a fluorescent moiety, and said receptor is an antibody or fragment thereof that binds to said fluorescent moiety.

30. A method according to claim 25, wherein said probe consists of a fluorescent moiety, and maid signal is a fluorescent signal generated from said probe.

31. A method according to claim 25, wherein said signal is a mass spectrum.

32. A method according to claim 25, wherein, prior to said proteolyzing step (c), one or more components of said complex protein mixture not bound to said probe are removed from said complex protein mixture.

33. A method according to claim 25, wherein said probe consists essentially of a label selected from the group consisting of a fluorescent moiety and a biotin moiety.

34. A method according to claim 25, wherein said separating step (e) comprises one or more separation methods selected from the group consisting of affinity separation, gel electrophoresis, capillary electrophoresis, liquid chromatography, HPLC, electrospray ionization mass spectrometry, MALDI mass spectrometry and combinations thereof.

35. A method according to claim 25, wherein prior to said proteolyzing step (c), said one or more active target proteins bound to said probe are bound to a solid support.

36. A method for comparing time presence, amount or activity of one or more active target proteins in each of two or more discrete proteomes, the method consisting of the sequential steps of:
   (a) contacting each of said discrete proteomes with a single activity based probe that binds predominantly to a single target site on one or more active target proteins, wherein the same activity based probe is used for each discrete proteome;
   (b) adding one or more standard proteins to said complex proteome mixture, wherein said standard protein(s) are optionally labeled with an activity based probe prior to addition to said complex protein mixture;
   (c) optionally removing from said complex protein mixture one or more components of said complex protein mixture not bound to said probe;
   (d) proteolyzing said discrete proteomes to produce a product mixture;
   (e) optionally binding said target protein(s) to a solid support;
   (f) separating each of said product mixtures into two or more components, one or more of which comprise peptides bound to said probe; and thereafter
   (g) comparing the presence, amount or activity of the active target proteins in each of the discrete proteomes by generating a signal from said one or more components comprising peptides bound to said probe.

37. A method according to claim 36, wherein said standard protein(s) are labeled with an activity based probe prior to addition to said complex protein mixture.

38. A method according to claim 37, wherein said activity based probe labeling said standard proteins consists of a fluorescent moiety that is distinguishable from said activity based probe contacted with complex protein mixture.

39. A method for detecting the presence, amount or activity of one or more active target proteins in a single complex protein mixture, the method consisting of the sequential steps of:
   (a) contacting said complex protein mixture with an activity based probe that specifically binds predominantly to a single target site on one or more active target protein;
   (b) optionally removing from said complex protein mixture one or more components of said complex protein mixture not bound to said probe;
   (c) proteolyzing said active target proteins to produce a product mixture;
   (d) optionally binding said target protein(s) to a solid support;
   (e) separating said product mixture into two or more components, one or more of which comprise peptides bound to said probe; and thereafter
   (f) generating a signal from said peptides bound to said probe, wherein the signal is correlated to the presence, amount, or activity of said one or more active target proteins in said complex protein mixture.

* * * * *